(12) United States Patent
Pearson et al.

(10) Patent No.: US 8,088,935 B2
(45) Date of Patent: Jan. 3, 2012

(54) COMPOUNDS AND METHODS FOR THE TREATMENT OF ASTHMA

(75) Inventors: James Pearson, Cambridge, MA (US); John J. Talley, Somerville, MA (US); Mark G. Currie, Sterling, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 1229 days.

(21) Appl. No.: 10/587,054

(22) PCT Filed: Dec. 23, 2004

(86) PCT No.: PCT/US2004/043082
§ 371 (c)(1),
(2), (4) Date: Nov. 22, 2006

(87) PCT Pub. No.: WO2005/063732
PCT Pub. Date: Jul. 14, 2005

(65) Prior Publication Data
US 2007/0249644 A1    Oct. 25, 2007

Related U.S. Application Data

(60) Provisional application No. 60/531,957, filed on Dec. 23, 2003.

(51) Int. Cl.
*C07D 311/22* (2006.01)
*A61K 31/353* (2006.01)

(52) U.S. Cl. .................. 549/401; 549/402; 514/456
(58) Field of Classification Search .................. 549/401, 549/402; 514/456
See application file for complete search history.

(56) References Cited

U.S. PATENT DOCUMENTS

| | | | |
|---|---|---|---|
| 3,790,580 A | 2/1974 | Johnson et al. | |
| 2003/0199529 A1 | 10/2003 | Garvey et al. | |

FOREIGN PATENT DOCUMENTS

| | | |
|---|---|---|
| DE | 2326227 | 2/1974 |
| ES | 398319 | 4/1975 |
| FR | 2196795 | 3/1974 |
| FR | 2196796 | 3/1974 |
| FR | 2210398 | 7/1974 |
| GB | 1297264 | 11/1972 |
| GB | 1374981 | 11/1974 |
| WO | 0193867 | 12/2001 |
| WO | 03080607 | 10/2003 |

OTHER PUBLICATIONS

Wang, 2002, Role of iNOS and eNOS in modulating proximal tubule transport and acid-base balance.*
Pizza et 1998. Nitric Oxide synthase inhition reduces muscle inflammation.*
Patrick Vallance 1998. Student BM.J.*

* cited by examiner

*Primary Examiner* — Rita Desai
(74) *Attorney, Agent, or Firm* — Heslin Rothenberg Farley & Mesiti P.C.

(57) ABSTRACT

Compounds and methods for the treatment of asthma are disclosed. The methods involve mast cell stabilization together with selective inhibition of iNOS. The compounds are combinations of a mast cell inhibiting moiety and an inhibitor of iNOS. An example is:

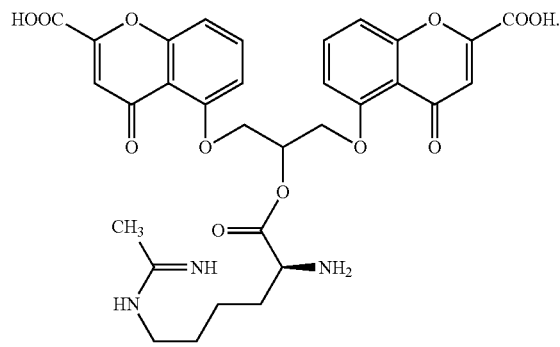

16 Claims, No Drawings

COMPOUNDS AND METHODS FOR THE TREATMENT OF ASTHMA

CROSS REFERENCE TO RELATED APPLICATIONS

This application is a 371 filing of PCT International Application No. PCT/US04/43082 filed Dec. 23, 2004, published in English as WO 2005/063732 on Jul. 14, 2005. PCT/US04/43082 claimed the priority of U.S. Provisional Application 60/531,957 filed Dec. 23, 2033. The disclosures of both are incorporated herein by reference in their entirety.

FIELD OF THE INVENTION

The invention relates to compounds and methods for the treatment of asthma. The methods involve mast cell stabilization together with selective inhibition of iNOS. The compounds are combinations of a mast cell inhibiting moiety and an inhibitor of iNOS.

BACKGROUND OF THE INVENTION

Asthma is a chronic airway inflammatory disorder characterized by bronchial hyper-reactivity and bronchospasm, among other abnormalities. Lungs of asthmatic patients have increased numbers of inflammatory cells in bronchioalveolar fluid and in lung tissues. These inflammatory cells include eosinophils, basophils, neutrophils, macrophages, and lymphocytes. In asthmatic lungs, the epithelium, including ciliated columnar epithelial cells, is damaged. IgE-antigen-mast cell interactions represent the early molecular and cellular events that cause inflammatory conditions of asthma.

Mast Cell Stabilizing Agents provide one approach to the prophylaxis and/or treatment of asthma. The prototype drug, disodium cromoglycate was synthesized in 1965 and was approved in the United States in 1973 as a prophylactic, nonbronchodilating anti-inflammatory drug for the therapy of allergic disorder. Cromolyn is an odorless, white, hygroscopic crystalline powder that is freely soluble in water up to 5%. Animal and human studies show it to be excreted unchanged in bile and urine. When inhaled into the pulmonary tree, as for treatment of asthma, only about 8% of a dose is deposited in the lung and absorbed. Peak plasma levels occur within 15 minutes, the biologic half-life is 46-99 minutes. Oral administration in humans results in approximately 1% being systemically absorbed. Cromolyn toxicity studies show an impressively low order of acute toxicity, and adverse effects tend to be minimal and reversible. Cromolyn has a unique, purely prophylactic action with no intrinsic bronchodilator or antihistaminic activity. Nedocromil was introduced subsequent to cromolyn. It is the other standard mast cell stabilizer used in the treatment of asthma. Its chemical properties and therapeutic characteristics are similar.

Nitric oxide (NO) is a diffusible radical involved in many physiological and pathological processes. It is synthesized in vivo by oxidation of L-arginine. The synthesis is catalyzed by a family of enzymes known as nitric oxide synthases or NO-synthases (NOSs), which are referenced in the international enzyme nomenclature system under the number E.C.1.14.13.39. Three NOS isoforms, two of which are constitutive and one inducible, are known:

(1) A neuronal NOS(NOS-1 or nNOS) was originally isolated and cloned from nerve tissue in which it is a constitutive enzyme. nNOS produces NO in response to various physiological stimuli, such as the activation of membrane receptors, according to a mechanism dependent on calcium and on calmodulin. nNOS-derived NO serves as a neurotransmitter.

(2) An inducible NOS(NOS-2 or iNOS) can be induced in response to immunological stimuli such as, for example, cytokines or bacterial antigens in various cells such as, for example macrophages, epithelial cells, hepatocytes, glial cells, and other cell types. The activity of this isoform is not regulated by calcium. Once induced, it produces large amounts of NO over prolonged periods.

(3) An endothelial NOS(NOS-3 or eNOS) is constitutive and calcium/calmodulin-dependent. It was originally identified in vascular endothelial cells, in which it generates NO in response to physiological stimuli such as the activation of membrane receptors.

Nitric oxide produced by eNOS and nNOS plays a critical role in cellular signaling and acts to control numerous physiologic functions including vasodilation and bronchodilation in the lung. In the asthmatic lung, eNOS and nNOS are downregulated, and thus contribute to edema and bronchoconstriction. Contemplating the problem of inadequate eNOS and nNOS activity, in an approach which is the opposite of that taken in the present invention, Garvey et al. (US published application 2003/0199529) have attached stimulators of endogenous NO production to mast cell inhibitors.

The NO produced in large amounts by the inducible isoform iNOS is involved in pathological phenomena associated with acute and chronic inflammatory processes in a large variety of tissues and organs. NO is highly reactive and, together with superoxide, forms peroxynitrite which damages tissues. In asthma this results in epithelial cell extrusion, sloughing, and cessation of cilia function. An excessive production of NO by induction of iNOS thus plays a part in degenerative pathologies with inflammatory components, such as asthma.

In conditions in which an overproduction of NO is deleterious, it would be desirable to reduce the production of NO by administering substances capable of inhibiting iNOS. However, given the important physiological roles played by the constitutive isoforms, selective inhibition of iNOS is required.

SUMMARY OF THE INVENTION

In a composition aspect, the invention relates to agents for treating a pulmonary disorder represented by the structure:

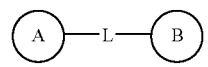

wherein
A is a mast-cell stabilizer;
L is a covalent linkage;
B is an iNOS inhibitor.

Examples of such agents are compounds of formula I or II

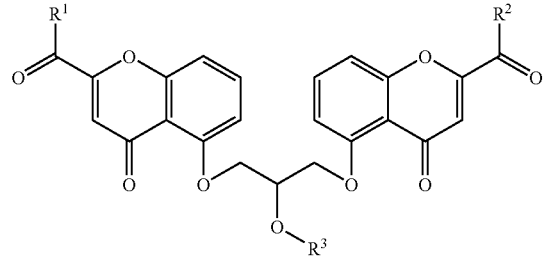

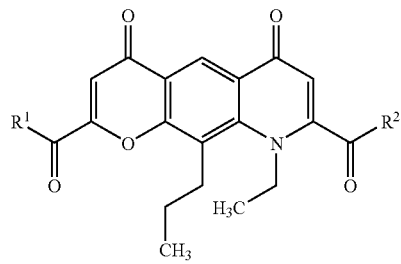

wherein
- $R^1$ and $R^2$ are chosen from hydroxy, $C_1$, $C_2$, $C_3$, $C_4$, $C_5$, and $C_6$ straight and branched alkoxy, -G-O(C=O)$R^4$, $R^5$, —NH$R^6$, —O$R^7$ and —O$^-$X$^+$, wherein X$^+$ is a pharmaceutically acceptable cation;
- $R^3$ is chosen from hydrogen, —(C=O)$R^4$, —(C=O)-G-O(C=O)$R^4$, —(C=O)$R^5$, —(C=O)NH$R^6$ and —(C=O)O$R^7$;
- —O(C=O)$R^4$ is the deshydrogen residue of a carboxylic acid, the parent of which, $R^4$COOH, is an inhibitor of inducible nitric oxide synthase (iNOS);
- —(C=O)$R^4$ is the deshydroxy residue of a carboxylic acid, the parent of which, $R^4$COOH, is an inhibitor of iNOS;
- $R^5$ is —O—$R^{20}$—U, wherein U is chosen from hydrogen, (1,2-dithiolan-3-yl) and phenyl, and $R^{20}$ is a divalent $C_1$ to $C_{20}$ alkane or oxaalkane residue;
- —NH$R^6$ is the deshydrogen residue of an amine, the parent of which, $R^6$NH$_2$, is an inhibitor of iNOS;
- —O$R^7$ is the deshydrogen residue of an alcohol, the parent of which, $R^7$OH, is an inhibitor of iNOS;
- G is a linking moiety cleavable under physiologic conditions. In the compounds of the invention, at least one of $R^1$, $R^2$ and $R^3$ must be -G-O(C=O)$R^4$, —$R^5$, —NH$R^6$, —O$R^7$, —(C=O)$R^4$, —(C=O)-G-O(C=O)$R^4$, —(C=O)$R^5$, —(C=O)NH$R^6$ or —(C=O)O$R^7$.

In another composition aspect, the invention relates to pharmaceutical compositions comprising a pharmaceutically acceptable carrier and a compound as described above.

In a method aspect the invention relates to a method for treating a pulmonary disorder comprising administering a compound represented by the structure:

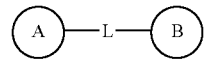

In a second method aspect, the invention relates to a method for treating a pulmonary disorder comprising co-administering a mast-cell stabilizer and an iNOS inhibitor in the form of a salt, in which one of the mast-cell stabilizer and the iNOS inhibitor is a cation or dication, and the other is an anion or dianion.

DETAILED DESCRIPTION OF THE INVENTION

Agents for treating a pulmonary disorder according to the invention are represented by the structure:

In one embodiment, L is chosen from —CONH—, —COO—, —O(C=O)O—, —O(C=O)NH—, —NH-CONH— and —(C=O)OCH(R)O(C=O)— and the compound is represented by a structure chosen from:

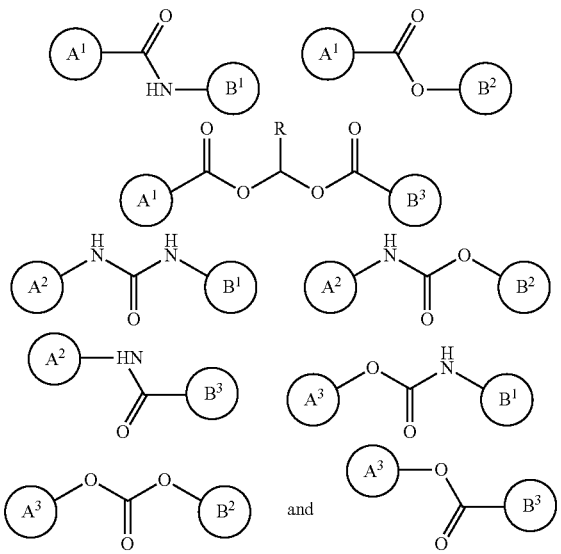

in which $A^1$ is a mast-cell stabilizer having a carboxylic acid substituent; $A^2$ is a mast-cell stabilizer having an amine substituent; $A^3$ is a mast-cell stabilizer having an alcohol substituent; $B^1$ is an iNOS inhibitor having an amine substituent; $B^2$ is an iNOS inhibitor having an alcohol substituent; $B^3$ is an iNOS inhibitor having a carboxylic acid substituent; and R is hydrogen or methyl. Cromolyn would be an example of a compound that fell into the categories $A^1$ (a mast-cell stabilizer having a carboxylic acid substituent) and $A^3$ (a mast-cell stabilizer having an alcohol substituent). Nedocromil would be an example of a compound that fell into category $A^1$. Numerous examples of compounds that fall in categories $B^1$, $B^2$ and $B^3$ are shown below as examples of parents of $R^4$.

In a particular embodiment, the compound is of formula I or II

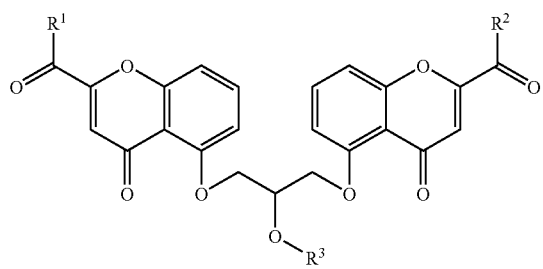

I

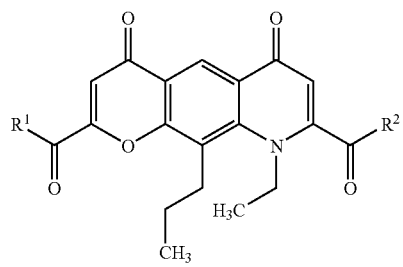

II

In these compounds

R¹ and R² are chosen from hydroxy, $C_1$, $C_2$, $C_3$, $C_4$, $C_5$, and $C_6$ straight and branched alkoxy, -G-O(C=O)R⁴, R⁵, —NHR⁶, —OR⁷ and —O⁻X⁺, wherein X⁺ is a pharmaceutically acceptable cation;

R³ is chosen from hydrogen, —(C=O)R⁴, —(C=O)-G-O(C=O)R⁴, —(C=O)R⁵, —(C=O)NHR⁶ and —(C=O)OR⁷;

—O(C=O)R⁴ is the deshydrogen residue of a carboxylic acid, the parent of which, R⁴COOH, is an inhibitor of inducible nitric oxide synthase (iNOS);

—(C=O)R⁴ is the deshydroxy residue of a carboxylic acid, the parent of which, R⁴COOH, is an inhibitor of iNOS;

R⁵ is —O—R²⁰—U, wherein U is chosen from hydrogen, (1,2-dithiolan-3-yl) and phenyl, and R²⁰ is a divalent $C_1$ to $C_{20}$ alkane or oxaalkane residue;

—NHR⁶ is the deshydrogen residue of an amine, the parent of which, R⁶NH₂, is an inhibitor of iNOS;

—OR⁷ is the deshydrogen residue of an alcohol, the parent of which, R⁷OH, is an inhibitor of iNOS;

G is a linking moiety cleavable under physiologic conditions.

Additional examples of such compounds include structures III through XI in which the R-groups retain the above definitions and R¹⁰ has the same definition as R¹ and R²:

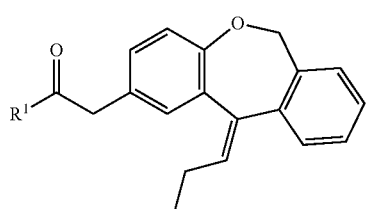

III

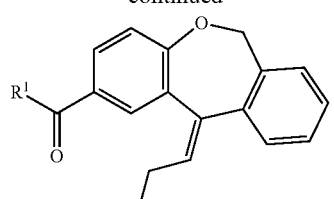

IV

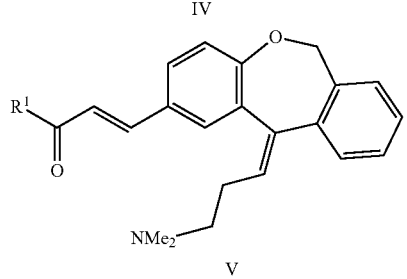

V

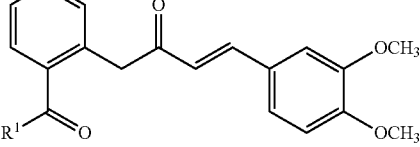

VI

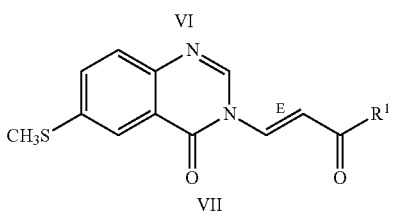

VII

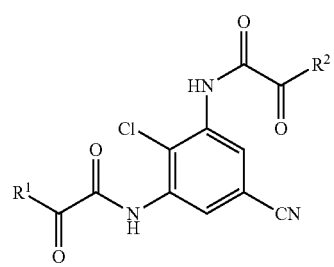

VIII

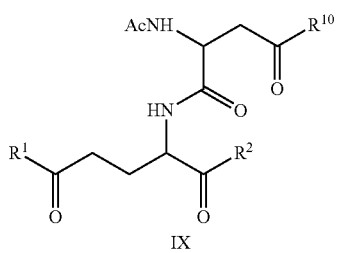

IX

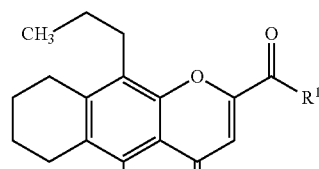

X

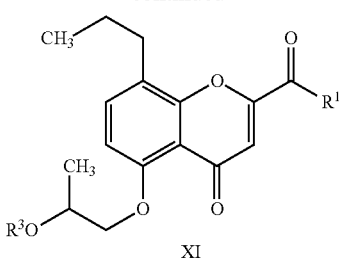
XI
Parents of the formulae R⁴COOH and R⁶NH₂ include:
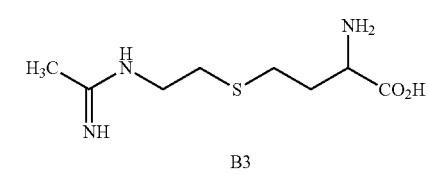
B1
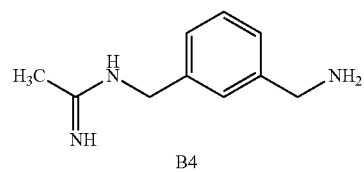
B2
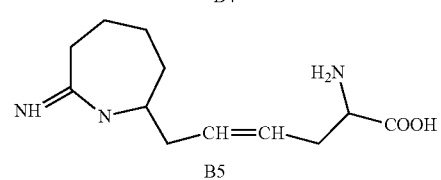
B3
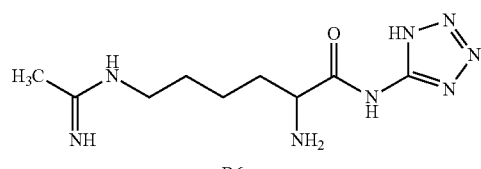
B4
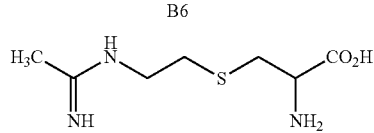
B5
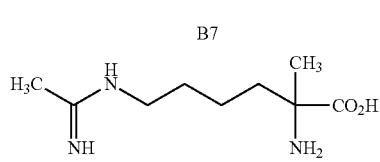
B6
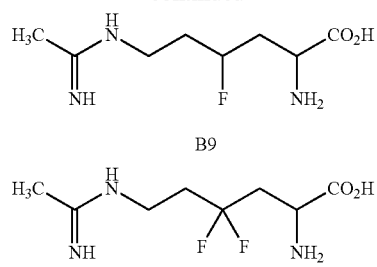
B7
B8
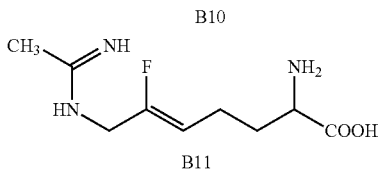
B9
B10
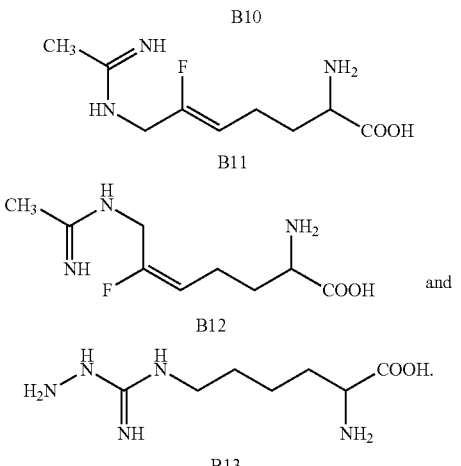
B11
B12
and
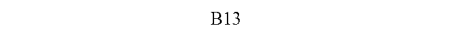
B13
Additional parents R⁶NH₂ may be chosen from compounds of structure:
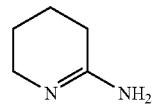
B14
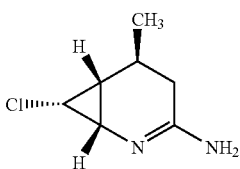
B15
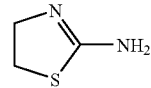
B16
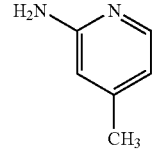
B17
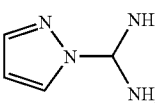
B18
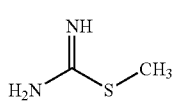
B19

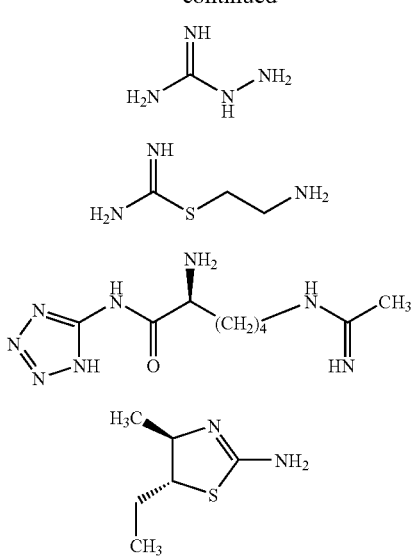

One parent of the formula $R^7OH$ is the iNOS-inhibitory alcohol B24 described in WO 98/37079 as example 53:

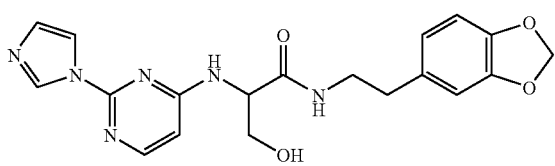

Additionally, parents of the formulae $R^4COOH$ and $R^6NH_2$ are chosen from the iNOS inhibitors described in U.S. Pat. No. 6,355,689:

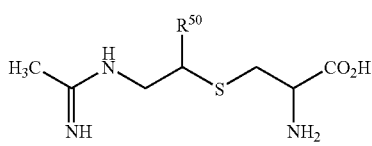

wherein $R^{50}$ is chosen from $C_1$ to $C_4$ alkyl, $C_3$ to $C_4$ cycloalkyl, $C_1$ to $C_4$ hydroxyalkyl and $C_1$ to $C_4$ haloalkyl or U.S. Pat. No. 5,863,931:

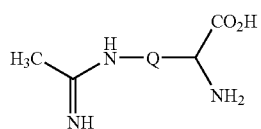

wherein Q is chosen from $—CH_2CH=CHCH_2—$, $—(CH_2)_pV(CH_2)_q$, $—O—$, $—NR^{51}—$ and $—(CH_2)_r T(CH_2)_s—$; p is 2 or 3; q is 1 or 2; V is $S(O)_x$; x is 0, 1 or 2; $R^{51}$ is H or $C_{1-6}$ alkyl; r is 1 or 2; s is 1 or 2; and T is cyclobutyl, phenyl or pyridyl. Other iNOS inhibitors useful as parent structures in the instant invention may be found in U.S. Pat. Nos. 6,451,821; 5,132,453; 5,830,917; 5,684,008; 6,207,708; 6,344,473; 6,143,790; 5,866,612; 6,369,272; 6,552,052; 6,495,544; 6,403,830; 5,629,322; 6,110,930; 6,228,866; 6,274,557; 6,432,947; 6,451,821; 5,449,688; 5,723,451; 5,854,251; 5,863,931; 5,889,056; 5,919,787; 5,945,408; 5,972,940; 5,981,511; 6,355,689; 6,423,705; 6,586,474 and 6,465,686; in US published applications 20030013702; 20020037927; 20020049202; 20030119826; 20020022631; 20020198243; 20030064978; 20030195256; 20030207896; 20030109522; 20040087653; in PCT applications WO99/62875; WO99/628785; WO01/78719; WO01/05748; WO01/14371; WO96/35677; WO96/33175; WO96/15120; WO95/11014; WO95/11231; WO95/25717; WO95/24382; WO94/12165; WO94/14780; WO93/13055; WO02/076395; WO03/097163; WO03/097050; WO03/026638; WO00/13709; WO00/26195; WO00/61126; WO01/00195; WO01/58867; WO01/74351; WO01/94325; WO02/00648; WO02/50021; WO93/05775; WO95/13805; WO95/34534; WO96/15120; WO96/27593; WO98/02555; WO98/37079; WO99/26657; WO99/46240; WO04/012726; WO01/72703; WO95/24832; WO94/12165; WO94/14780; WO04/106312 and WO03/026668 and in European published applications EPO446699; EP1299365; EP765308; EP957087 and EP1282413. The relevant disclosures of all are incorporated herein by reference.

The concept of "parent", as used herein, refers to a compound, such as B1

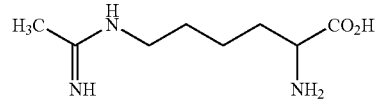

which is a selective inhibitor of iNOS. When the residue of this parent is attached to a chroman of formula I, one possible resulting structure is 512:

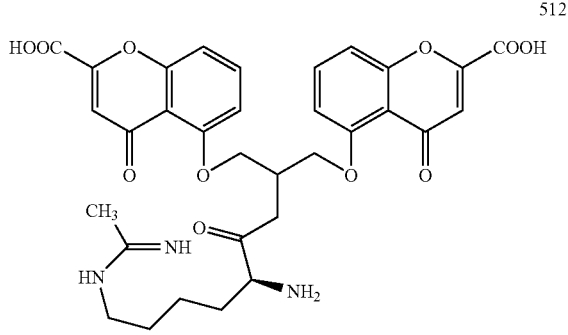

in which $R^3$ is $—(C=O)R^4$ and $—(C=O)R^4$ is the deshydroxy residue of a carboxylic acid, the parent of which, B1, is an inhibitor of iNOS. It will be immediately apparent that B1 could also be attached to I as an amide:

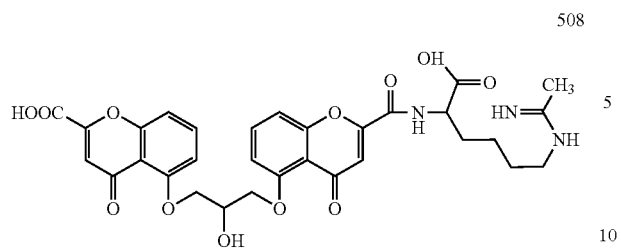

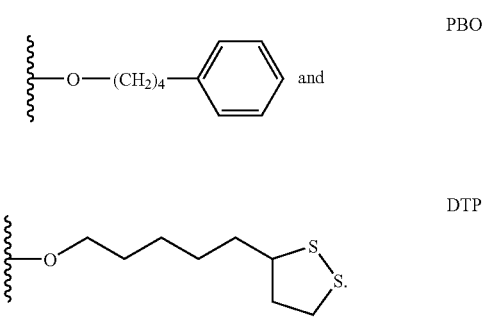

in which case $R^2$ is —$NHR^6$ and —$NHR^6$ is the deshydrogen residue of an amine, the parent of which, B1, is an inhibitor of iNOS. Similarly, alcohols may be attached as esters:

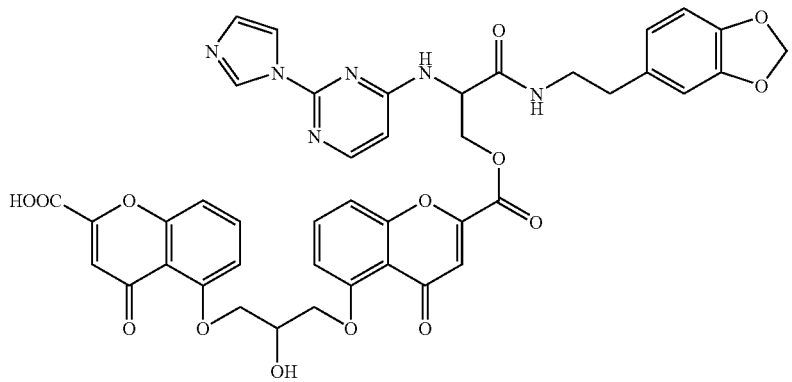

In one subgenus, $R^1$ and $R^2$ are chosen from hydroxy, $C_1$, $C_2$, $C_3$, $C_4$, $C_5$, and $C_6$ straight and branched alkoxy, —$R^5$, —$NHR^6$, —$OR^7$ and —$O^-X^+$; and $R^3$ is chosen from hydrogen, —(C=O)$R^4$, —(C=O)$R^5$, —(C=O)$NHR^6$ and —(C=O)$OR^7$. Another genus includes compounds of formula:

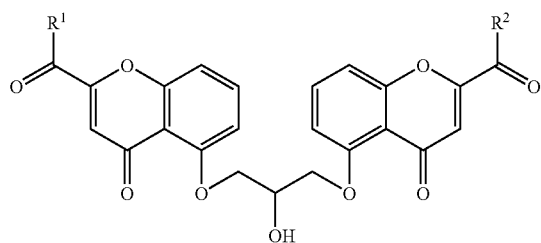

in which $R^1$ is chosen from -G-O(C=O)$R^4$, —$NHR^6$ and $OR^7$; and $R^2$ is chosen from hydroxy, $C_1$, $C_2$, $C_3$, $C_4$, $C_5$, and $C_6$ straight and branched alkoxy, $R^5$ and —$O^-X$.

In another subgenus at least one of $R^1$, $R^2$ and $R^3$ is -G-O(C=O)$R^4$ or —(C=O)-G-O(C=O)$R^4$; and G is chosen from —$OCH_2$— and —$OCH(CH_3)$—. "G" in these cases forms an acetal of formaldehyde or acetaldehyde with the oxygen of —O(C=O)$R^4$. Acetals are particularly suitable as linkers that are readily cleaved under physiological conditions.

$R^5$ substituents include straight or branched alkyl groups of 1, 2, 3, 4, 5 and 6 carbon atoms, PBO and DTP:

In other subgenera the compounds are dioxo-4H,6H-pyrano [3,2-g]quinolines

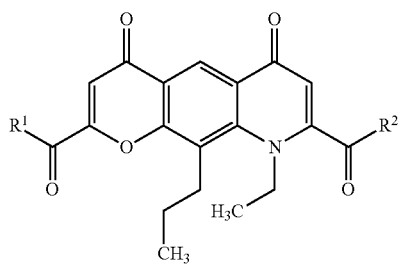

wherein $R^1$ is chosen from hydroxy, $R^5$ and —$O^-X$; and $R^2$ is chosen from -G-O(C=O)$R^4$, —$NHR^6$ and $OR^7$ or wherein $R^1$ is chosen from -G-O(C=O)$R^4$, —$NHR^6$ and $OR^7$; and $R^2$ is chosen from hydroxy, $R^5$ and —$O^-X$.

Other subgenera include esters of formula

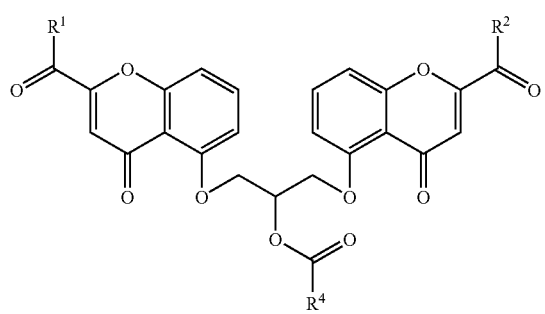

wherein $R^1$ and $R^2$ are chosen from hydroxy, $C_1$, $C_2$, $C_3$, $C_4$, $C_5$, and $C_6$ straight and branched alkoxy and —O⁻X⁺; and esters of formula

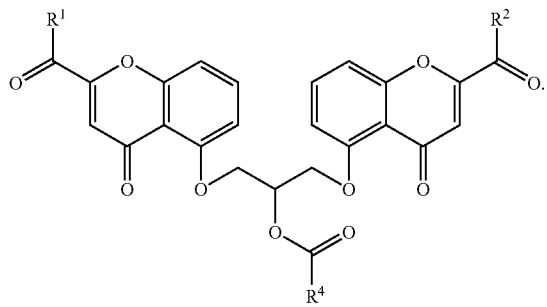

The compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

The configuration of any carbon-carbon double bond appearing herein is selected for convenience only and, unless a specific configuration is expressly indicated, the depiction is not intended to designate a particular configuration; thus a carbon-carbon double bond depicted arbitrarily herein as E may be Z, E, or a mixture of the two in any proportion.

As used herein, and as would be understood by the person of skill in the art, the recitation of "a compound" is intended to include salts and solvates of that compound.

The term "solvate" refers to a compound in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Compounds of formula I may contain basic or acidic residues, allowing them to be presented as salts. The term "pharmaceutically acceptable salt" refers to salts whose counter ion (anion) derives from pharmaceutically acceptable non-toxic acids and bases. When the compounds contain a quat or a basic residue, suitable pharmaceutically acceptable base addition salts for the compounds of the present invention include inorganic acids, organic acids and, in the case of quats, water (which formally furnishes the hydroxide anion). Examples include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate, and the like. When the compounds contain an acidic residue, suitable pharmaceutically acceptable base addition salts for the compounds of the present invention include ammonium, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Other base addition salts includes those made from: arecoline, arginine, barium, benethamine, benzathine, betaine, bismuth, clemizole, copper, deanol, diethylamine, diethylaminoethanol, epolamine, ethylenediamine, ferric, ferrous, glucamine, glucosamine, histidine, hydrabamine, imidazole, isopropylamine, manganic, manganous, methylglucamine, morpholine, morpholineethanol, N-ethylmorpholine, N-ethylpiperidine, piperazine, piperidine, polyamine resins, purines, theobromine, triethylamine, trimethylamine, tripropylamine, trolamine, and tromethamine.

DEFINITIONS

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Methyl is preferred. Preferred alkyl and alkylene groups are those of $C_{20}$ or below (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$). Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon includes alkyl, cycloalkyl, alkenyl, alkynyl, aryl and combinations thereof. Examples include benzyl, phenethyl, cyclohexylmethyl, camphoryl and naphthylethyl.

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1, 2, 3, 4, 5, 6, 7 or 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. Aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

A "quaternary ammonium salt" as used herein refers to a substituent of the general formula —$N^+R^7R^8R^9X^-$, in which $R^7$ is $C_1$ to $C_{20}$ hydrocarbon or forms a five- to seven-membered ring with $R^8$; $R^8$ is alkyl or forms a five- to seven-membered ring with $R^7$; $R^9$ is alkyl or together with $R^7$ or $R^8$ forms a second five- to seven-membered ring; and X is an anion.

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage of the acetals "G") or through the intermediacy of enzymes in the respiratory system, for example by esterases within the alveoli.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Throughout this application, various references are referred to. The disclosures of these publications in their entireties are hereby incorporated by reference as if written herein.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans. Humans would be the preferred subjects of the methods of treatment.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991].

The abbreviations Me, Et, Ph, Tf, Ts and Ms represent methyl, ethyl, phenyl, trifluoromethanesulfonyl, toluenesulfonyl and methanesulfonyl respectively. For example, in the tables, OEt refers to ethoxy. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The invention also encompasses pharmaceutical compositions comprising a pharmaceutically acceptable carrier and the foregoing compounds. One embodiment of the invention includes aerosol pharmaceutical compositions. Another embodiment of the invention includes oral formulations including tablets, capsules and syrups.

While it may be possible for the compounds to be administered as the raw chemical, it is preferable to present them as a pharmaceutical composition. According to a further aspect, the present invention provides a pharmaceutical composition comprising a compound as described above, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Formulations suitable for pulmonary route inhalation include sterile solutions for nebulization comprising a therapeutically effective amount of the compound dissolved in aqueous saline solution and optionally containing a preservative such as benzalkonium chloride or chlorobutanol, and aerosol formulations comprising a therapeutically effective amount dissolved or suspended in an appropriate propellant. Aerosols (e.g., jet or ultrasonic nebulizers, metered-dose inhalers (MDIs), and dry-powder inhalers (DPIs)) can also be used in intranasal applications. Aerosols may be conveniently presented in unit dosage form and prepared by any of the methods well-known in the art of pharmacy. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants, which include but are not limited to bile salts and those described in U.S. Pat. No. 6,524,557 and references therein. The surfactants described in U.S. Pat. No. 6,524,557, e.g., a C8-C16 fatty acid salt, a bile salt, a phospholipid, or alkyl saccharide are advantageous in that some of them also reportedly enhance absorption of the compound in the formulation.

Also suitable in the invention are dry powder formulations comprising a therapeutically effective amount of active compound blended with an appropriate carrier and adapted for use in connection with a dry-powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. No. 5,230,884, U.S. Pat. No. 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, U.S. Pat. No. 6,436, 367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

While the pulmonary route is advantageous in most instances, there may also be instances in which other routes of administration may be advantageous. For example, oral administration may be desirable. In that regard, one may contemplate administration using a formulation in which the compound is releasably encapsulated by modified amino acids, as described in U.S. Pat. No. 5,811,127. One may also contemplate administration as an implantable sustained-release dosage form, such as described in US published application 20040115236.

The dose range for adult humans is generally from 0.005 mg to 10 g/day orally. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

The invention also relates to methods for preventing and/or treating pulmonary disorders. According to the invention one may administer a compound as described above for treating bronchospasm, for inducing bronchodilation, for treating chronic obstructive pulmonary disease (including chronic bronchitis with normal airflow), for treating asthma (including allergen-induced asthma, viral-induced asthma, cold-induced asthma, pollution-induced asthma and exercise-induced asthma) and for treating rhinitis (including allergic rhinitis).

A broad spectrum of respiratory diseases and disorders have been recognized, many of which have overlapping and interacting etiologies. One of the most widespread and prevalent of these diseases in western populations is the chronic disease referred to as "asthma". Other such disorders are also characterized by acute pulmonary vasoconstriction such as may result from pneumonia, traumatic injury, aspiration or inhalation injury, fat embolism in the lung, acidosis inflammation of the lung, adult respiratory distress syndrome, acute pulmonary edema, acute mountain sickness, post-cardiac surgery, acute pulmonary hypertension, persistent pulmonary hypertension of the newborn, perinatal aspiration syndrome, hyaline membrane disease, acute pulmonary thromboembolism, herapin-protamine reactions, sepsis, status asthmaticus or hypoxia (including iatrogenic hypoxia) and other forms of reversible pulmonary vasoconstriction. Such pulmonary disorders also are also characterized by inflammation of the lung including those associated with the migration into the lung of nonresident cell types including the various leucocyte subclasses. Also included in the respiratory disorders contemplated are: bullous disease, pigeon fancier's disease, asthmatic bronchitis, chronic bronchitis with airway obstruction (chronic obstructive bronchitis), emphysema, farmer's lung, allergic eye diseases (including allergic conjunctivitis, vernal conjunctivitis, vernal keratoconjunctivitis, and giant papillary conjunctivitis), and cystic fibrosis and other diseases which are characterized by inflammation of the lung and/or excess mucosal secretion. Other physiological events which are contemplated to be controlled include platelet activation in the lung.

The methods for treating pulmonary disorders also encompass co-administering a mast-cell stabilizer and an iNOS inhibitor in the form of a salt, in which one of the mast-cell stabilizer and the iNOS inhibitor is a cation or dication, and the other is an anion or dianion.

Cations include:

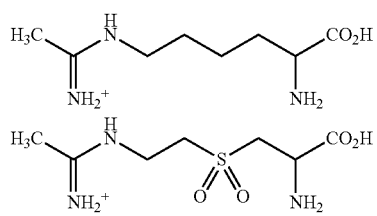

-continued

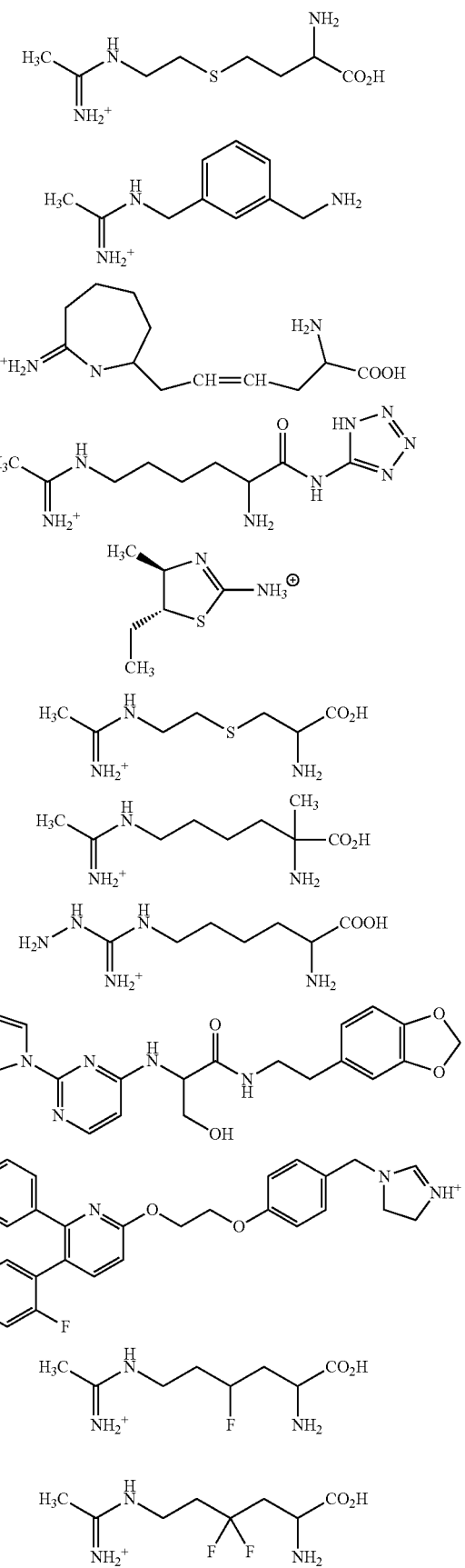

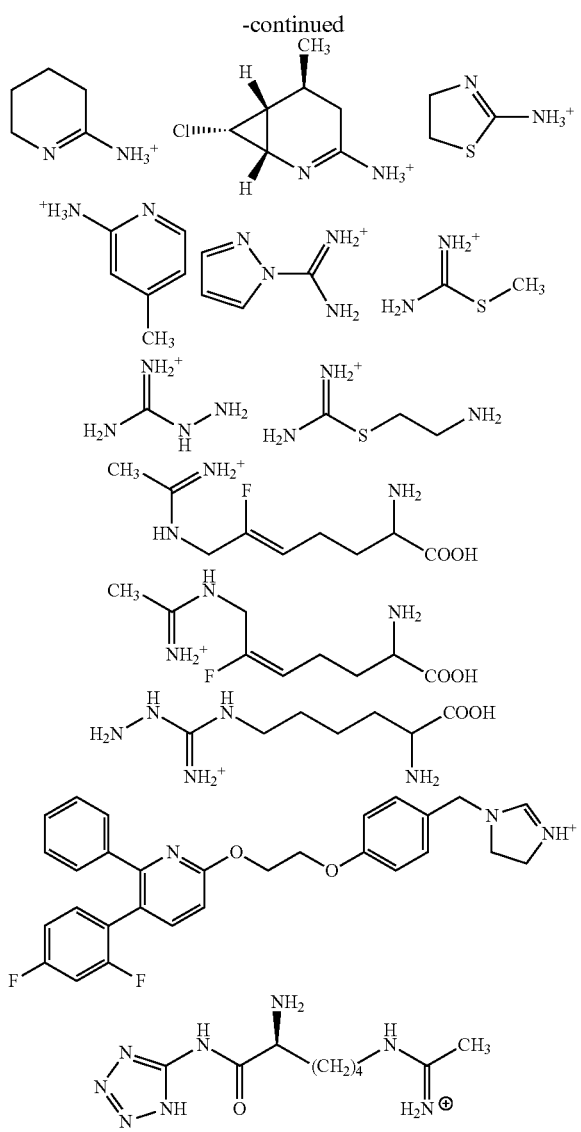
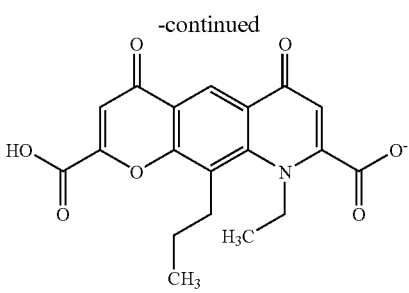

and their corresponding dications. Anions include:

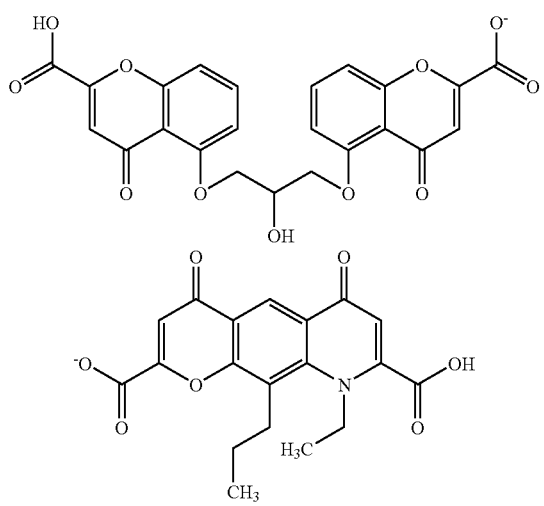

and their corresponding dianions.

The invention also encompasses the salts themselves.

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The compounds of the present invention can be coadministered with any of the following: (1) β-agonists including but not limited to: albuterol (Proventil®, Salbutamol®, Ventolin®), bambuterol, bitoterol, clenbuterol, fenoterol, formoterol, isoetharine (Bronkosol®, Bronkometer®), metaproterenol (Alupent®, Metaprel®), pirbuterol (Maxair®), reproterol, rimiterol, salmeterol, terbutaline (Brethaire®, Brethine®, Bricanyl®), adrenalin, isoproterenol (Isuprel®), epinephrine bitartrate (Primatene®), ephedrine, orciprenline, fenoterol and isoetharine; (2) steroids, including but not limited to beclomethasone, beclomethasone dipropionate, betamethasone, budesonide, bunedoside, butixocort, dexamethasone, flunisolide, fluocortin, fluticasone, hydrocortisone, methyl prednisone, mometasone, predonisolone, predonisone, tipredane, tixocortal, triamcinolone, and triamcinolone acetonide; (3) β-agonist-corticosteroid combinations [e.g., salmeterol-fluticasone (Advair®), formoterol-budesonid (Symbicort®)]; (4) leukotriene D4 receptor antagonists/ leukotriene antagonists/LTD4 antagonists (i.e., any compound that is capable of blocking, inhibiting, reducing or otherwise interrupting the interaction between leukotrienes and the Cys LTI receptor) including but not limited to: zafirlukast, montelukast, montelukast sodium (Singulair®), pranlukast, iralukast, pobilukast, SKB-106,203 and compounds described as having LTD4 antagonizing activity described in U.S. Pat. No. 5,565,473; (5) 5-lipoxygenase inhibitors and/or leukotriene biosynthesis inhibitors [e.g.

zileuton and BAY1005 (CA registry 128253-31-6)]; (6) histamine H1 receptor antagonists/antihistamines (i.e. any compound that is capable of blocking, inhibiting, reducing or otherwise interrupting the interaction between histamine and its receptor) including but not limited to: astemizole, acrivastine, antazoline, azatadine, azelastine, astamizole, bromopheniramine, bromopheniramine maleate, carbinoxamine, carebastine, cetirizine, chlorpheniramine, chlorpheniramine maleate, cimetidine, clemastine, cyclizine, cyproheptadine, descarboethoxyloratadine, dexchlorpheniramine, dimethindene, diphenhydramine, diphenylpyraline, doxylamine succinate, doxylamine, ebastine, efletirizine, epinastine, famotidine, fexofenadine, hydroxyzine, hydroxyzine, ketotifen, levocabastine, levocetirizine, levocetirizine, loratadine, meclizine, mepyramine, mequitazine, methdilazine, mianserin, mizolastine, noberastine, norasternizole, noraztemizole, phenindamine, pheniramine, picumast, promethazine, pynlamine, pyrilamine, ranitidine, temelastine, terfenadine, trimeprazine, tripelenamine, and triprolidine; (7) an anticholinergic including but not limited to: atropine, benztropine, biperiden, flutropium, hyoscyamine, ilutropium, ipratropium, ipratropium bromide, methscopolamine, oxybutinin, rispenzepine, scopolamine, and tiotropium; (8) an antitussive including but not limited to: dextromethorphan, codeine, and hydromorphone; (9) a decongestant including but not limited to: pseudoephedrine and phenylpropanolamine; (10) an expectorant including but not limited to: guafenesin, guaicolsulfate, terpin, ammonium chloride, glycerol guaicolate, and iodinated glycerol; (11) a bronchodilator including but not limited to: theophylline and aminophylline; (12) an anti-inflammatory including but not limited to: fluribiprofen, diclophenac, indomethacin, ketoprofen, S-ketroprophen, tenoxicam; (13) a PDE inhibitor including but not limited to filaminast, denbufyllene piclamilast, roflumilast, zardaverine, and rolipram; (14) a recombinant humanized monoclonal antibody [e.g. xolair (also called omalizumab), rhuMab, and talizumab]; and (14) a humanized lung surfactant [e.g. Surtaxin®, formerly known as dsc-104 (Discovery Laboratories)].

Finally one may describe the compounds of formula I or II

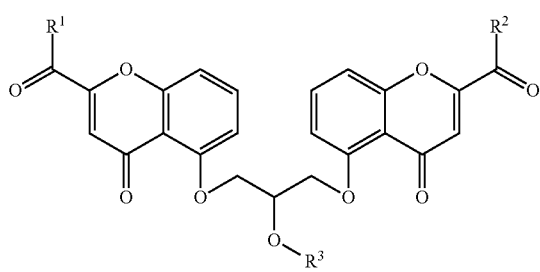

I

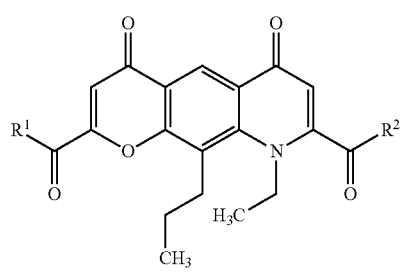

II in means-plus-function terms. In other words, —O(C=O)R$^4$ is the deshydrogen residue of a carboxylic acid, the parent of which, R$^4$COOH, is a chemical means for inhibiting inducible nitric oxide synthase (iNOS);

—(C=O)R$^4$ is the deshydroxy residue of a carboxylic acid, the parent of which, R$^4$COOH, is a chemical means for inhibiting iNOS;

—NHR$^6$ is the deshydrogen residue of an amine, the parent of which, R$^6$NH$_2$, is a chemical means for inhibiting iNOS;

—OR$^7$ is the deshydrogen residue of an alcohol, the parent of which, R$^7$OH, is a chemical means for inhibiting iNOS.

Chemical means for inhibiting iNOS are compounds (i.e. chemicals) that exhibit IC$_{50}$ below 25 µM when tested against human iNOS according to the method of Moore et al. *J. Med. Chem.* 39, 669-672 (1996). Examples of many such compounds are shown above as B1 through B24. In one embodiment, inhibitors are those with IC$_{50}$ below 10 µM. In another embodiment, inhibitors are those with an IC$_{50}$ below 5 µM. For the purpose of the invention, iNOS inhibitors should be selective for iNOS over eNOS and nNOS. Selective means having an IC$_{50}$ against iNOS that is no more than $\frac{1}{10}^{th}$ the IC$_{50}$ against nNOS and eNOS as measured by the method described in Moore (op. cit.) Unless some other meaning is clear from its context, the term "iNOS inhibitor", not further modified, as used herein refers to a selective iNOS inhibitor.

The compounds of the present invention may possess one or more of the following advantages: they lessen bronchial epithelial damage in asthma; they exhibit improved stability, formulation and manufacturing characteristics; they possess improved pharmacokinetic properties, allowing in many cases, once or twice daily inhaled dosing; they offer an alternative to steroid therapy The efficacy of the compounds of the invention may be demonstrated in a test that measures airway hyperresponsiveness [see Muijsers et al. *Br. J. Pharmacol.* 134, 434 (2001); Elwood et al. *Am. Rev. Respir. Dis.* 145, 1289-1294 (1992) and Eynott et al. *Eur. J. Pharm.* 452, 123 (2002)] or in a test that measures inflammation in an airway [see Chen et al. *Acta Pharmacol. Sin.* 24, 697 (2003)]. The activity of the compounds of the invention can be tested in the presence or absence of serum. In the presence of serum, one would expect both iNOS activity and mast cell stabilization activity, which can be assayed in methods described by Misko et al. [*Eur. J. Pharmacol.* 233, 119-125 (1993)] and Kusner et al. [*J. Pharmacol. Exp. Ther.* 184, 41-46 (1973)] respectively.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

In Scheme I disodium chromylglycate 1 is treated with one equivalent of an alkyl halide in a dipolar aprotic solvent such as dimethylformamide (DMF) to provide the corresponding mono-ester 2. Typically, this procedure also produces some diester 3, wherein R1=R2 and unreacted 1. After separation of the mono-ester 2 it can be converted into diester 3 by reaction with an alkyl halide in a dipolar aprotic solvent to provide the diester 3. The diester 3 is then condensed with an appropriately protected acid, such as an N-Boc-amino acid inhibitor of iNOS, in the presence of a dehydrating agent, such as 1,3-dicyclohexylcarbodiimide (DCC), to provide the protected ester. The protecting group is then removed to provide the desired chromyl iNOS inhibitors 4. In the case of an N-Boc-amino acid, the protecting group can be removed by an acid such as HCl in dioxane.

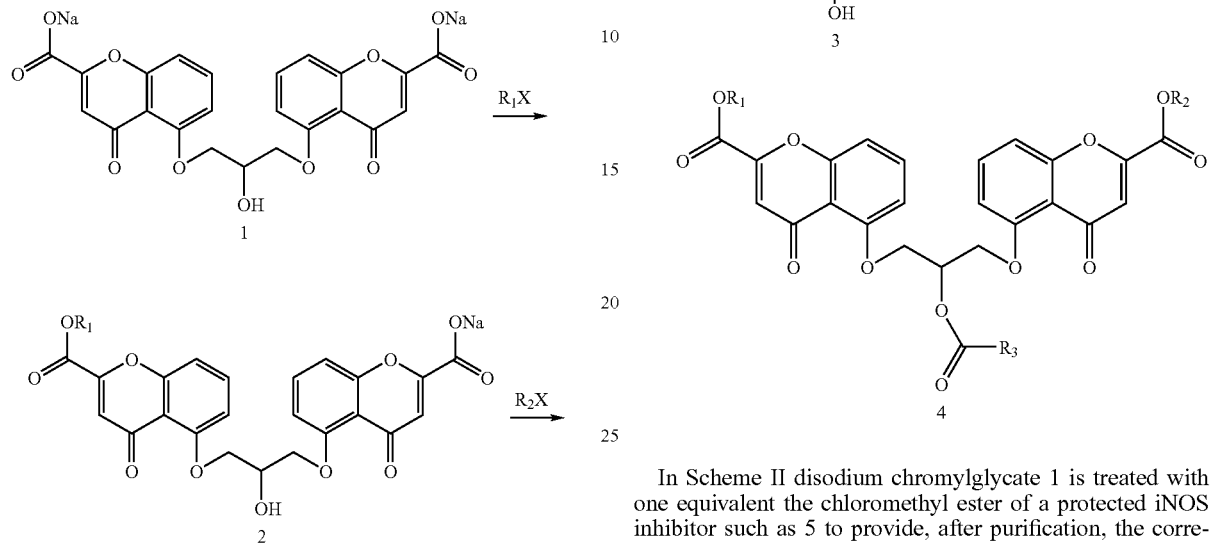

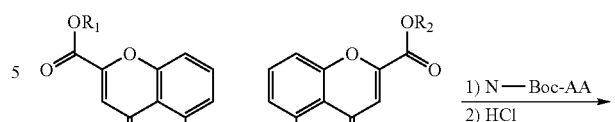

In Scheme II disodium chromylglycate 1 is treated with one equivalent the chloromethyl ester of a protected iNOS inhibitor such as 5 to provide, after purification, the corresponding ester. The ester is then deprotected to afford the desired chromyl iNOS inhibitor 6.

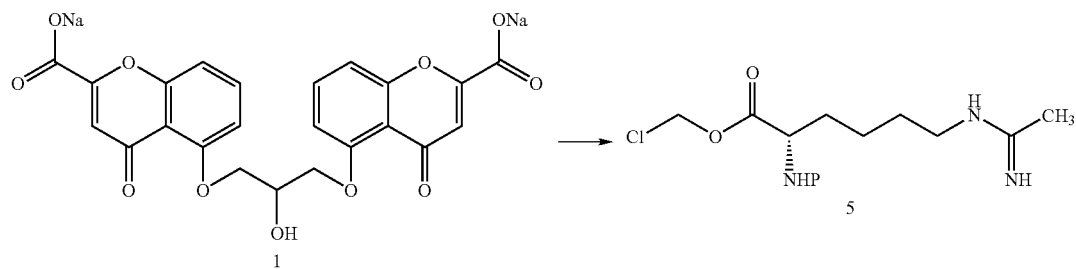

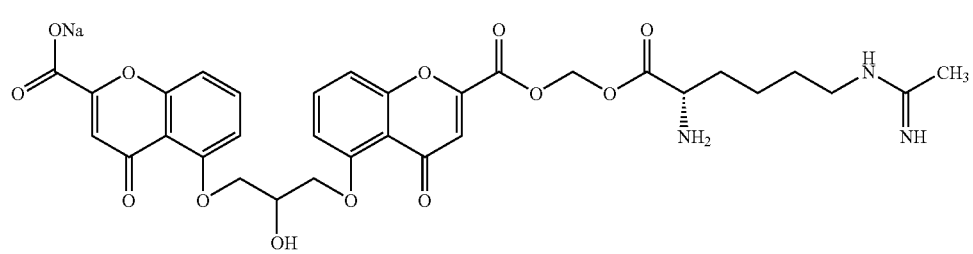

Scheme III illustrates the method for the preparation of mono-ester amide derivatives 8. The route commences with the coupling of an orthogonally protected ester of an iNOS inhibitor 7 with the mono-ester 2 in the presence of a amide coupling agent such as 1,3-dicyclohexylcarbodiimide. The resulting amide derivative is then converted into the desired analogues 8 by removal of the ester of the iNOS moiety. The ester moiety of the iNOS inhibitor can be such things as the tert-butyl ester, the beta-trimethylsilylethyl ester, para-methoxybenzyl ester, and the like. If the iNOS inhibitor component does not possess an acid substituent then the amine can be coupled directly to 2 without the need for protection and deprotection. If the desired product is the free acid of 8 ($R^1$=H) the route can be to saponify the ester of 8, or to couple one equivalent of the protected iNOS inhibitor 7 with 1 followed by removal of the protecting groups.

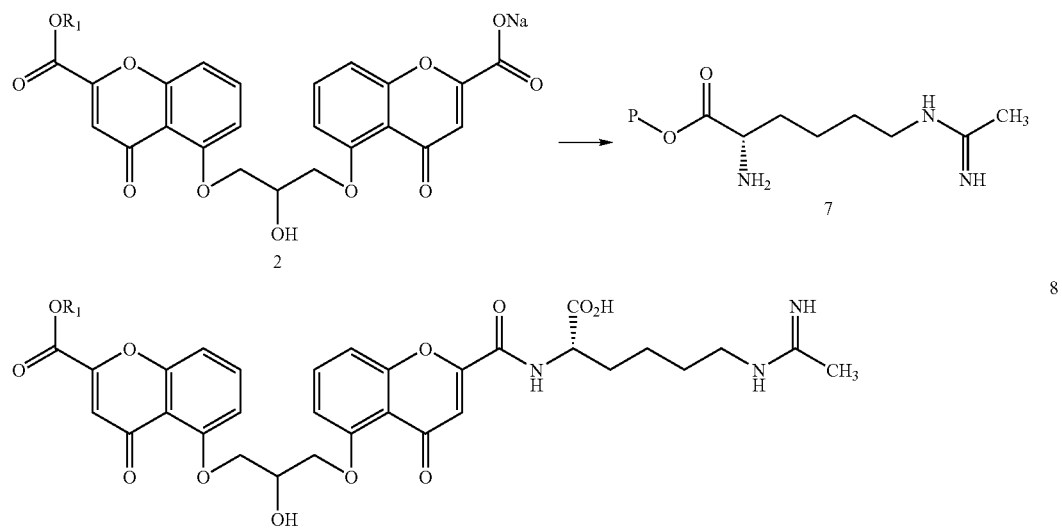

Illustrated in Scheme IV is the method used for the preparation of bis-iNOS amides of chromyln. The method involves coupling of 1 with the ester protected iNOS inhibitor moiety 7 in the presence of a dehydrating agent such as 1,3-dicyclohexylcarbodiimide to produce the ester protected version of 9, R=ester. In a subsequent step the ester moiety is converted to the corresponding acid, 9, R=H, by saponification. Suitable esters are those listed in Scheme III.

Compounds that are representative of the invention are shown in Tables 1 and 2 below. In these tables the numbers and abbreviations refer to structures presented above. Thus, for example, the compound of example 111 in Table 1 is described as an amide of B1 and an ester of PBO attached to the nedocromil core. The structure of the compound would be:

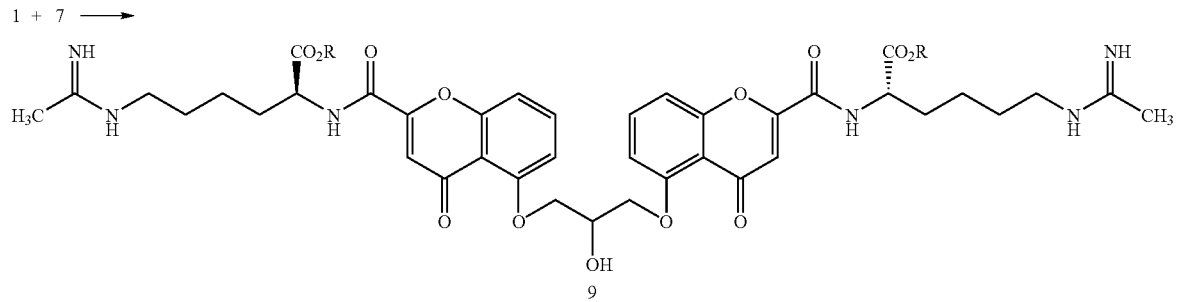

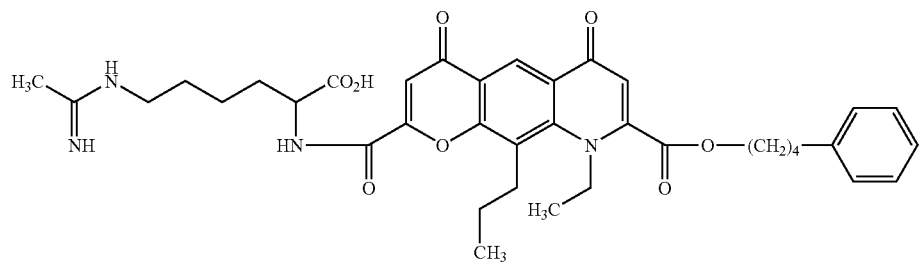

111

In all of the compounds in the tables, when an amide is formed, it is formed from the primary α-amine when $R^1$ or $R^2$ is an α-amino acid (B1-B3, B5, B7-B13), and from the primary amine or amidine in the other cases (B4, B6, B14-B19, B22, B23). When the residue is B20, the point of attachment is on the terminal nitrogen of the hydrazine; when the residue is B21, the point of attachment is the primary amine. The entry "acetal" in the columns headed "linkage" refer to acetals of formaldehyde, i.e. —OCH$_2$O—. Thus the compound of example 518 in Table 2 has the structure:

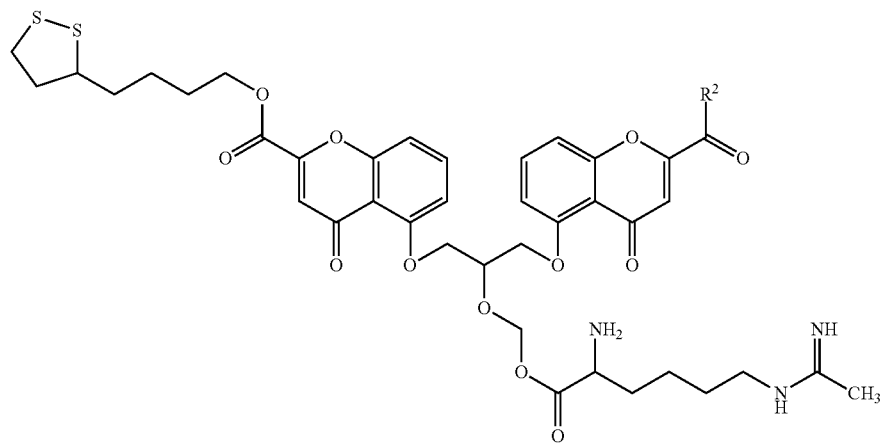

518

TABLE 1

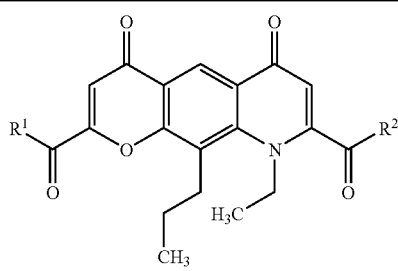

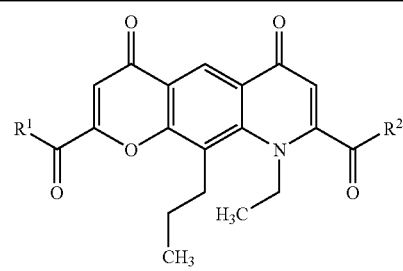

TABLE 1-continued

| Example # | R1 | linkage | R2 | linkage | Example # | R1 | linkage | R2 | linkage |
|---|---|---|---|---|---|---|---|---|---|
| 100 | B1 | ester | —OH | n/a | 108 | B1 | amide | —OH | n/a |
| 101 | B1 | ester | —OEt | ester | 109 | B1 | amide | —OEt | ester |
| 102 | B1 | ester | DTP | ester | 110 | B1 | amide | DTP | ester |
| 103 | B1 | ester | PBO | ester | 111 | B1 | amide | PBO | ester |
| 104 | B1 | acetal | —OH | n/a | 112 | —OH | n/a | B1 | ester |
| 105 | B1 | acetal | —OEt | ester | 113 | —OEt | ester | B1 | ester |
| 106 | B1 | acetal | DTP | ester | 114 | DTP | ester | B1 | ester |
| 107 | B1 | acetal | PBO | ester | 115 | PBO | ester | B1 | ester |

TABLE 1-continued

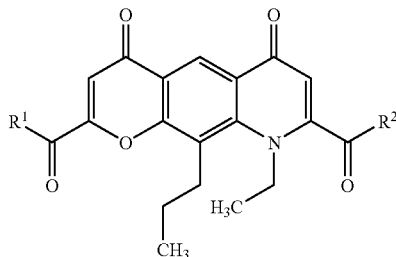

| Example # | R1 | linkage | R2 | linkage |
|---|---|---|---|---|
| 116 | —OH | n/a | B1 | acetal |
| 117 | —OEt | ester | B1 | acetal |
| 118 | DTP | ester | B1 | acetal |
| 119 | PBO | ester | B1 | acetal |
| 120 | —OH | n/a | B1 | amide |
| 121 | —OEt | ester | B1 | amide |
| 122 | DTP | ester | B1 | amide |
| 123 | PBO | ester | B1 | amide |
| 124 | B2 | ester | —OH | n/a |
| 125 | B2 | ester | —OEt | ester |
| 126 | B2 | ester | DTP | ester |
| 127 | B2 | ester | PBO | ester |
| 128 | B2 | acetal | —OH | n/a |
| 129 | B2 | acetal | —OEt | ester |
| 130 | B2 | acetal | DTP | ester |
| 131 | B2 | acetal | PBO | ester |
| 132 | B2 | amide | —OH | n/a |
| 133 | B2 | amide | —OEt | ester |
| 134 | B2 | amide | DTP | ester |
| 135 | B2 | amide | PBO | ester |
| 136 | —OH | n/a | B2 | ester |
| 137 | —OEt | ester | B2 | ester |
| 138 | DTP | ester | B2 | ester |
| 139 | PBO | ester | B2 | ester |
| 140 | —OH | n/a | B2 | acetal |
| 141 | —OEt | ester | B2 | acetal |
| 142 | DTP | ester | B2 | acetal |
| 143 | PBO | ester | B2 | acetal |
| 144 | —OH | n/a | B2 | amide |
| 145 | —OEt | ester | B2 | amide |
| 146 | DTP | ester | B2 | amide |
| 147 | PBO | ester | B2 | amide |
| 148 | B3 | ester | —OH | n/a |
| 149 | B3 | ester | —OEt | ester |
| 150 | B3 | ester | DTP | ester |
| 151 | B3 | ester | PBO | ester |
| 152 | B3 | acetal | —OH | n/a |
| 153 | B3 | acetal | —OEt | ester |
| 154 | B3 | acetal | DTP | ester |
| 155 | B3 | acetal | PBO | ester |
| 156 | B3 | amide | —OH | n/a |
| 157 | B3 | amide | —OEt | ester |
| 158 | B3 | amide | DTP | ester |
| 159 | B3 | amide | PBO | ester |
| 160 | —OH | n/a | B3 | ester |
| 161 | —OEt | ester | B3 | ester |
| 162 | DTP | ester | B3 | ester |
| 163 | PBO | ester | B3 | ester |
| 164 | —OH | n/a | B3 | acetal |
| 165 | —OEt | ester | B3 | acetal |
| 166 | DTP | ester | B3 | acetal |
| 167 | PBO | ester | B3 | acetal |
| 168 | —OH | n/a | B3 | amide |
| 169 | —OEt | ester | B3 | amide |
| 170 | DTP | ester | B3 | amide |
| 171 | PBO | ester | B3 | amide |
| 172 | B4 | amide | —OH | n/a |
| 173 | B4 | amide | —OEt | ester |
| 174 | B4 | amide | DTP | ester |
| 175 | B4 | amide | PBO | ester |
| 176 | —OH | n/a | B4 | amide |
| 177 | —OEt | ester | B4 | amide |
| 178 | DTP | ester | B4 | amide |
| 179 | PBO | ester | B4 | amide |

TABLE 1-continued

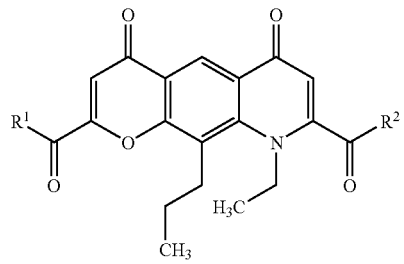

| Example # | R1 | linkage | R2 | linkage |
|---|---|---|---|---|
| 180 | B5 | ester | —OH | n/a |
| 181 | B5 | ester | —OEt | ester |
| 182 | B5 | ester | DTP | ester |
| 183 | B5 | ester | PBO | ester |
| 184 | B5 | acetal | —OH | n/a |
| 185 | B5 | acetal | —OEt | ester |
| 186 | B5 | acetal | DTP | ester |
| 187 | B5 | acetal | PBO | ester |
| 188 | B5 | amide | —OH | n/a |
| 189 | B5 | amide | —OEt | ester |
| 190 | B5 | amide | DTP | ester |
| 191 | B5 | amide | PBO | ester |
| 192 | —OH | n/a | B5 | ester |
| 193 | —OEt | ester | B5 | ester |
| 194 | DTP | ester | B5 | ester |
| 195 | PBO | ester | B5 | ester |
| 196 | —OH | n/a | B5 | acetal |
| 197 | —OEt | ester | B5 | acetal |
| 198 | DTP | ester | B5 | acetal |
| 199 | PBO | ester | B5 | acetal |
| 200 | —OH | n/a | B5 | amide |
| 201 | —OEt | ester | B5 | amide |
| 202 | DTP | ester | B5 | amide |
| 203 | PBO | ester | B5 | amide |
| 204 | B6 | amide | —OH | n/a |
| 205 | B6 | amide | —OEt | ester |
| 206 | B6 | amide | DTP | ester |
| 207 | B6 | amide | PBO | ester |
| 208 | —OH | n/a | B6 | amide |
| 209 | —OEt | ester | B6 | amide |
| 210 | DTP | ester | B6 | amide |
| 211 | PBO | ester | B6 | amide |
| 212 | B7 | ester | —OH | n/a |
| 213 | B7 | ester | —OEt | ester |
| 214 | B7 | ester | DTP | ester |
| 215 | B7 | ester | PBO | ester |
| 216 | B7 | acetal | —OH | n/a |
| 217 | B7 | acetal | —OEt | ester |
| 218 | B7 | acetal | DTP | ester |
| 219 | B7 | acetal | PBO | ester |
| 220 | B7 | amide | —OH | n/a |
| 221 | B7 | amide | —OEt | ester |
| 222 | B7 | amide | DTP | ester |
| 223 | B7 | amide | PBO | ester |
| 224 | —OH | n/a | B7 | ester |
| 225 | —OEt | ester | B7 | ester |
| 226 | DTP | ester | B7 | ester |
| 227 | PBO | ester | B7 | ester |
| 228 | —OH | n/a | B7 | acetal |
| 229 | —OEt | ester | B7 | acetal |
| 230 | DTP | ester | B7 | acetal |
| 231 | PBO | ester | B7 | acetal |
| 232 | —OH | n/a | B7 | amide |
| 233 | —OEt | ester | B7 | amide |
| 234 | DTP | ester | B7 | amide |
| 235 | PBO | ester | B7 | amide |
| 236 | B8 | ester | —OH | n/a |
| 237 | B8 | ester | —OEt | ester |
| 238 | B8 | ester | DTP | ester |
| 239 | B8 | ester | PBO | ester |
| 240 | B8 | acetal | —OH | n/a |
| 241 | B8 | acetal | —OEt | ester |
| 242 | B8 | acetal | DTP | ester |
| 243 | B8 | acetal | PBO | ester |

TABLE 1-continued

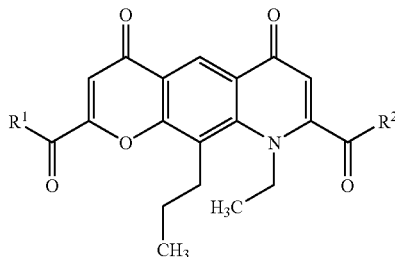

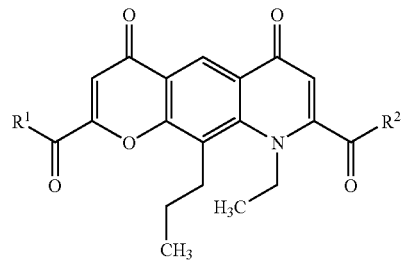

| Example # | R1 | linkage | R2 | linkage |
|---|---|---|---|---|
| 244 | B8 | amide | —OH | n/a |
| 245 | B8 | amide | —OEt | ester |
| 246 | B8 | amide | DTP | ester |
| 247 | B8 | amide | PBO | ester |
| 248 | —OH | n/a | B8 | ester |
| 249 | —OEt | ester | B8 | ester |
| 250 | DTP | ester | B8 | ester |
| 251 | PBO | ester | B8 | ester |
| 252 | —OH | n/a | B8 | acetal |
| 253 | —OEt | ester | B8 | acetal |
| 254 | DTP | ester | B8 | acetal |
| 255 | PBO | ester | B8 | acetal |
| 256 | —OH | n/a | B8 | amide |
| 257 | —OEt | ester | B8 | amide |
| 258 | DTP | ester | B8 | amide |
| 259 | PBO | ester | B8 | amide |
| 260 | B9 | ester | —OH | n/a |
| 261 | B9 | ester | —OEt | ester |
| 262 | B9 | ester | DTP | ester |
| 263 | B9 | ester | PBO | ester |
| 264 | B9 | acetal | —OH | n/a |
| 265 | B9 | acetal | —OEt | ester |
| 266 | B9 | acetal | DTP | ester |
| 267 | B9 | acetal | PBO | ester |
| 268 | B9 | amide | —OH | n/a |
| 269 | B9 | amide | —OEt | ester |
| 270 | B9 | amide | DTP | ester |
| 271 | B9 | amide | PBO | ester |
| 272 | —OH | n/a | B9 | ester |
| 273 | —OEt | ester | B9 | ester |
| 274 | DTP | ester | B9 | ester |
| 275 | PBO | ester | B9 | ester |
| 276 | —OH | n/a | B9 | acetal |
| 277 | —OEt | ester | B9 | acetal |
| 278 | DTP | ester | B9 | acetal |
| 279 | PBO | ester | B9 | acetal |
| 280 | —OH | n/a | B9 | amide |
| 281 | —OEt | ester | B9 | amide |
| 282 | DTP | ester | B9 | amide |
| 283 | PBO | ester | B9 | amide |
| 284 | B10 | ester | —OH | n/a |
| 285 | B10 | ester | —OEt | ester |
| 286 | B10 | ester | DTP | ester |
| 287 | B10 | ester | PBO | ester |
| 288 | B10 | acetal | —OH | n/a |
| 289 | B10 | acetal | —OEt | ester |
| 290 | B10 | acetal | DTP | ester |
| 291 | B10 | acetal | PBO | ester |
| 292 | B10 | amide | —OH | n/a |
| 293 | B10 | amide | —OEt | ester |
| 294 | B10 | amide | DTP | ester |
| 295 | B10 | amide | PBO | ester |
| 296 | —OH | n/a | B10 | ester |
| 297 | —OEt | ester | B10 | ester |
| 298 | DTP | ester | B10 | ester |
| 299 | PBO | ester | B10 | ester |
| 300 | —OH | n/a | B10 | acetal |
| 301 | —OEt | ester | B10 | acetal |
| 302 | DTP | ester | B10 | acetal |
| 303 | PBO | ester | B10 | acetal |
| 304 | —OH | n/a | B10 | amide |
| 305 | —OEt | ester | B10 | amide |
| 306 | DTP | ester | B10 | amide |
| 307 | PBO | ester | B10 | amide |
| 308 | B11 | ester | —OH | n/a |
| 309 | B11 | ester | —OEt | ester |
| 310 | B11 | ester | DTP | ester |
| 311 | B11 | ester | PBO | ester |
| 312 | B11 | acetal | —OH | n/a |
| 313 | B11 | acetal | —OEt | ester |
| 314 | B11 | acetal | DTP | ester |
| 315 | B11 | acetal | PBO | ester |
| 316 | B11 | amide | —OH | n/a |
| 317 | B11 | amide | —OEt | ester |
| 318 | B11 | amide | DTP | ester |
| 319 | B11 | amide | PBO | ester |
| 320 | —OH | n/a | B11 | ester |
| 321 | —OEt | ester | B11 | ester |
| 322 | DTP | ester | B11 | ester |
| 323 | PBO | ester | B11 | ester |
| 324 | —OH | n/a | B11 | acetal |
| 325 | —OEt | ester | B11 | acetal |
| 326 | DTP | ester | B11 | acetal |
| 327 | PBO | ester | B11 | acetal |
| 328 | —OH | n/a | B11 | amide |
| 329 | —OEt | ester | B11 | amide |
| 330 | DTP | ester | B11 | amide |
| 331 | PBO | ester | B11 | amide |
| 332 | B12 | ester | —OH | n/a |
| 333 | B12 | ester | —OEt | ester |
| 334 | B12 | ester | DTP | ester |
| 335 | B12 | ester | PBO | ester |
| 336 | B12 | acetal | —OH | n/a |
| 337 | B12 | acetal | —OEt | ester |
| 338 | B12 | acetal | DTP | ester |
| 339 | B12 | acetal | PBO | ester |
| 340 | B12 | amide | —OH | n/a |
| 341 | B12 | amide | —OEt | ester |
| 342 | B12 | amide | DTP | ester |
| 343 | B12 | amide | PBO | ester |
| 344 | —OH | n/a | B12 | ester |
| 345 | —OEt | ester | B12 | ester |
| 346 | DTP | ester | B12 | ester |
| 347 | PBO | ester | B12 | ester |
| 348 | —OH | n/a | B12 | acetal |
| 349 | —OEt | ester | B12 | acetal |
| 350 | DTP | ester | B12 | acetal |
| 351 | PBO | ester | B12 | acetal |
| 352 | —OH | n/a | B12 | amide |
| 353 | —OEt | ester | B12 | amide |
| 354 | DTP | ester | B12 | amide |
| 355 | PBO | ester | B12 | amide |
| 356 | B13 | ester | —OH | n/a |
| 357 | B13 | ester | —OEt | ester |
| 358 | B13 | ester | DTP | ester |
| 359 | B13 | ester | PBO | ester |
| 360 | B13 | acetal | —OH | n/a |
| 361 | B13 | acetal | —OEt | ester |
| 362 | B13 | acetal | DTP | ester |
| 363 | B13 | acetal | PBO | ester |
| 364 | B13 | amide | —OH | n/a |
| 365 | B13 | amide | —OEt | ester |
| 366 | B13 | amide | DTP | ester |
| 367 | B13 | amide | PBO | ester |
| 368 | —OH | n/a | B13 | ester |
| 369 | —OEt | ester | B13 | ester |
| 370 | DTP | ester | B13 | ester |
| 371 | PBO | ester | B13 | ester |

TABLE 1-continued

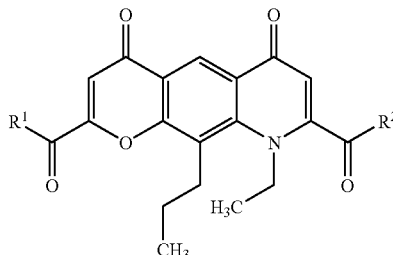

| Example # | R1 | linkage | R2 | linkage |
|---|---|---|---|---|
| 372 | —OH | n/a | B13 | acetal |
| 373 | —OEt | ester | B13 | acetal |
| 374 | DTP | ester | B13 | acetal |
| 375 | PBO | ester | B13 | acetal |
| 376 | —OH | n/a | B13 | amide |
| 377 | —OEt | ester | B13 | amide |
| 378 | DTP | ester | B13 | amide |
| 379 | PBO | ester | B13 | amide |
| 380 | B14 | amide | —OH | n/a |
| 381 | B14 | amide | —OEt | ester |
| 382 | B14 | amide | DTP | ester |
| 383 | B14 | amide | PBO | ester |
| 384 | —OH | n/a | B14 | amide |
| 385 | —OEt | ester | B14 | amide |
| 386 | DTP | ester | B14 | amide |
| 387 | PBO | ester | B14 | amide |
| 388 | B15 | amide | —OH | n/a |
| 389 | B15 | amide | —OEt | ester |
| 390 | B15 | amide | DTP | ester |
| 391 | B15 | amide | PBO | ester |
| 392 | —OH | n/a | B15 | amide |
| 393 | —OEt | ester | B15 | amide |
| 394 | DTP | ester | B15 | amide |
| 395 | PBO | ester | B15 | amide |
| 396 | B16 | amide | —OH | n/a |
| 397 | B16 | amide | —OEt | ester |
| 398 | B16 | amide | DTP | ester |
| 399 | B16 | amide | PBO | ester |
| 400 | —OH | n/a | B16 | amide |
| 401 | —OEt | ester | B16 | amide |
| 402 | DTP | ester | B16 | amide |
| 403 | PBO | ester | B16 | amide |
| 404 | B17 | amide | —OH | n/a |
| 405 | B17 | amide | —OEt | ester |
| 406 | B17 | amide | DTP | ester |
| 407 | B17 | amide | PBO | ester |
| 408 | —OH | n/a | B17 | amide |
| 409 | —OEt | ester | B17 | amide |
| 410 | DTP | ester | B17 | amide |
| 411 | PBO | ester | B17 | amide |
| 412 | B18 | amide | —OH | n/a |
| 413 | B18 | amide | —OEt | ester |
| 414 | B18 | amide | DTP | ester |
| 415 | B18 | amide | PBO | ester |
| 416 | —OH | n/a | B18 | amide |
| 417 | —OEt | ester | B18 | amide |
| 418 | DTP | ester | B18 | amide |
| 419 | PBO | ester | B18 | amide |
| 420 | B19 | amide | —OH | n/a |
| 421 | B19 | amide | —OEt | ester |
| 422 | B19 | amide | DTP | ester |
| 423 | B19 | amide | PBO | ester |
| 424 | —OH | n/a | B19 | amide |
| 425 | —OEt | ester | B19 | amide |
| 426 | DTP | ester | B19 | amide |
| 427 | PBO | ester | B19 | amide |
| 428 | B20 | amide | —OH | n/a |
| 429 | B20 | amide | —OEt | ester |
| 430 | B20 | amide | DTP | ester |
| 431 | B20 | amide | PBO | ester |
| 432 | —OH | n/a | B20 | amide |
| 433 | —OEt | ester | B20 | amide |
| 434 | DTP | ester | B20 | amide |
| 435 | PBO | ester | B20 | amide |

TABLE 1-continued

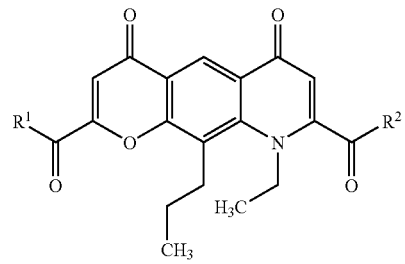

| Example # | R1 | linkage | R2 | linkage |
|---|---|---|---|---|
| 436 | B21 | amide | —OH | n/a |
| 437 | B21 | amide | —OEt | ester |
| 438 | B21 | amide | DTP | ester |
| 439 | B21 | amide | PBO | ester |
| 440 | —OH | n/a | B21 | amide |
| 441 | —OEt | ester | B21 | amide |
| 442 | DTP | ester | B21 | amide |
| 443 | PBO | ester | B21 | amide |
| 444 | B22 | amide | —OH | n/a |
| 445 | B22 | amide | —OEt | ester |
| 446 | B22 | amide | DTP | ester |
| 447 | B22 | amide | PBO | ester |
| 448 | —OH | n/a | B22 | amide |
| 449 | —OEt | ester | B22 | amide |
| 450 | DTP | ester | B22 | amide |
| 451 | PBO | ester | B22 | amide |
| 452 | B23 | amide | —OH | n/a |
| 453 | B23 | amide | —OEt | ester |
| 454 | B23 | amide | DTP | ester |
| 455 | B23 | amide | PBO | ester |
| 456 | —OH | n/a | B23 | amide |
| 457 | —OEt | ester | B23 | amide |
| 458 | DTP | ester | B23 | amide |
| 459 | PBO | ester | B23 | amide |
| 460 | B24 | ester | —OH | n/a |
| 461 | B24 | ester | —OEt | ester |
| 462 | B24 | ester | DTP | ester |
| 463 | B24 | ester | PBO | ester |
| 464 | —OH | n/a | B24 | ester |
| 465 | —OEt | ester | B24 | ester |
| 466 | DTP | ester | B24 | ester |
| 467 | PBO | ester | B24 | ester |

TABLE 2

| Example # | R1 | linkage | R2 | linkage | R3 | linkage |
|---|---|---|---|---|---|---|
| 500 | B1 | ester | —OH | n/a | —H | n/a |
| 501 | B1 | ester | —OEt | ester | —H | n/a |
| 502 | B1 | ester | DTP | ester | —H | n/a |
| 503 | B1 | ester | PBO | ester | —H | n/a |
| 504 | B1 | acetal | —OH | n/a | —H | n/a |
| 505 | B1 | acetal | —OEt | ester | —H | n/a |
| 506 | B1 | acetal | DTP | ester | —H | n/a |
| 507 | B1 | acetal | PBO | ester | —H | n/a |
| 508 | B1 | amide | —OH | n/a | —H | n/a |
| 509 | B1 | amide | —OEt | ester | —H | n/a |
| 510 | B1 | amide | DTP | ester | —H | n/a |
| 511 | B1 | amide | PBO | ester | —H | n/a |

TABLE 2-continued

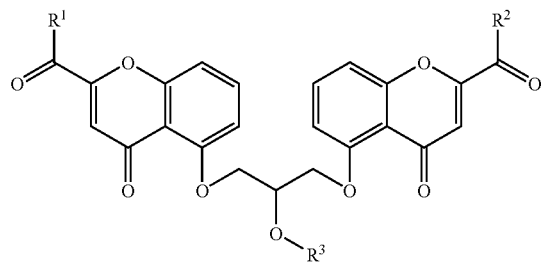

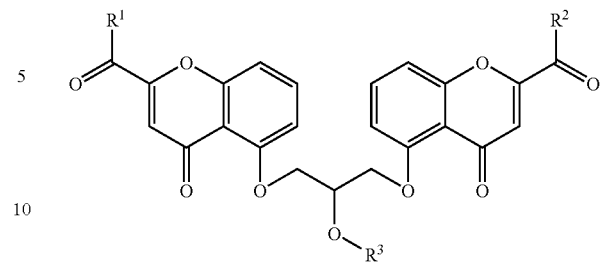

| Example # | R1 | linkage | R2 | linkage | R3 | linkage |
|---|---|---|---|---|---|---|
| 512 | —OH | n/a | —OH | n/a | B1 | ester |
| 513 | —OEt | ester | —OH | n/a | B1 | ester |
| 514 | DTP | ester | —OH | n/a | B1 | ester |
| 515 | PBO | ester | —OH | n/a | B1 | ester |
| 516 | —OH | n/a | —OH | n/a | B1 | acetal |
| 517 | —OEt | ester | —OH | n/a | B1 | acetal |
| 518 | DTP | ester | —OH | n/a | B1 | acetal |
| 519 | PBO | ester | —OH | n/a | B1 | acetal |
| 520 | B2 | ester | —OH | n/a | —H | n/a |
| 521 | B2 | ester | —OEt | ester | —H | n/a |
| 522 | B2 | ester | DTP | ester | —H | n/a |
| 523 | B2 | ester | PBO | ester | —H | n/a |
| 524 | B2 | acetal | —OH | n/a | —H | n/a |
| 525 | B2 | acetal | —OEt | ester | —H | n/a |
| 526 | B2 | acetal | DTP | ester | —H | n/a |
| 527 | B2 | acetal | PBO | ester | —H | n/a |
| 528 | B2 | amide | —OH | n/a | —H | n/a |
| 529 | B2 | amide | —OEt | ester | —H | n/a |
| 530 | B2 | amide | DTP | ester | —H | n/a |
| 531 | B2 | amide | PBO | ester | —H | n/a |
| 532 | —OH | n/a | —OH | n/a | B2 | ester |
| 533 | —OEt | ester | —OH | n/a | B2 | ester |
| 534 | DTP | ester | —OH | n/a | B2 | ester |
| 535 | PBO | ester | —OH | n/a | B2 | ester |
| 536 | —OH | n/a | —OH | n/a | B2 | acetal |
| 537 | —OEt | ester | —OH | n/a | B2 | acetal |
| 538 | DTP | ester | —OH | n/a | B2 | acetal |
| 539 | PBO | ester | —OH | n/a | B2 | acetal |
| 540 | B3 | ester | —OH | n/a | —H | n/a |
| 541 | B3 | ester | —OEt | ester | —H | n/a |
| 542 | B3 | ester | DTP | ester | —H | n/a |
| 543 | B3 | ester | PBO | ester | —H | n/a |
| 544 | B3 | acetal | —OH | n/a | —H | n/a |
| 545 | B3 | acetal | —OEt | ester | —H | n/a |
| 546 | B3 | acetal | DTP | ester | —H | n/a |
| 547 | B3 | acetal | PBO | ester | —H | n/a |
| 548 | B3 | amide | —OH | n/a | —H | n/a |
| 549 | B3 | amide | —OEt | ester | —H | n/a |
| 550 | B3 | amide | DTP | ester | —H | n/a |
| 551 | B3 | amide | PBO | ester | —H | n/a |
| 552 | —OH | n/a | —OH | n/a | B3 | ester |
| 553 | —OEt | ester | —OH | n/a | B3 | ester |
| 554 | DTP | ester | —OH | n/a | B3 | ester |
| 555 | PBO | ester | —OH | n/a | B3 | ester |
| 556 | —OH | n/a | —OH | n/a | B3 | acetal |
| 557 | —OEt | ester | —OH | n/a | B3 | acetal |
| 558 | DTP | ester | —OH | n/a | B3 | acetal |
| 559 | PBO | ester | —OH | n/a | B3 | acetal |
| 560 | B4 | amide | —OH | n/a | —H | n/a |
| 561 | B4 | amide | —OEt | ester | —H | n/a |
| 562 | B4 | amide | DTP | ester | —H | n/a |
| 563 | B4 | amide | PBO | ester | —H | n/a |
| 564 | B5 | ester | —OH | n/a | —H | n/a |
| 565 | B5 | ester | —OEt | ester | —H | n/a |
| 566 | B5 | ester | DTP | ester | —H | n/a |
| 567 | B5 | ester | PBO | ester | —H | n/a |
| 568 | B5 | acetal | —OH | n/a | —H | n/a |
| 569 | B5 | acetal | —OEt | ester | —H | n/a |
| 570 | B5 | acetal | DTP | ester | —H | n/a |
| 571 | B5 | acetal | PBO | ester | —H | n/a |
| 572 | B5 | amide | —OH | n/a | —H | n/a |
| 573 | B5 | amide | —OEt | ester | —H | n/a |
| 574 | B5 | amide | DTP | ester | —H | n/a |
| 575 | B5 | amide | PBO | ester | —H | n/a |
| 576 | —OH | n/a | —OH | n/a | B5 | ester |
| 577 | —OEt | ester | —OH | n/a | B5 | ester |
| 578 | DTP | ester | —OH | n/a | B5 | ester |
| 579 | PBO | ester | —OH | n/a | B5 | ester |
| 580 | —OH | n/a | —OH | n/a | B5 | acetal |
| 581 | —OEt | ester | —OH | n/a | B5 | acetal |
| 582 | DTP | ester | —OH | n/a | B5 | acetal |
| 583 | PBO | ester | —OH | n/a | B5 | acetal |
| 584 | B6 | amide | —OH | n/a | —H | n/a |
| 585 | B6 | amide | —OEt | ester | —H | n/a |
| 586 | B6 | amide | DTP | ester | —H | n/a |
| 587 | B6 | amide | PBO | ester | —H | n/a |
| 588 | B7 | ester | —OH | n/a | —H | n/a |
| 589 | B7 | ester | —OEt | ester | —H | n/a |
| 590 | B7 | ester | DTP | ester | —H | n/a |
| 591 | B7 | ester | PBO | ester | —H | n/a |
| 592 | B7 | acetal | —OH | n/a | —H | n/a |
| 593 | B7 | acetal | —OEt | ester | —H | n/a |
| 594 | B7 | acetal | DTP | ester | —H | n/a |
| 595 | B7 | acetal | PBO | ester | —H | n/a |
| 596 | B7 | amide | —OH | n/a | —H | n/a |
| 597 | B7 | amide | —OEt | ester | —H | n/a |
| 598 | B7 | amide | DTP | ester | —H | n/a |
| 599 | B7 | amide | PBO | ester | —H | n/a |
| 600 | —OH | n/a | —OH | n/a | B7 | ester |
| 601 | —OEt | ester | —OH | n/a | B7 | ester |
| 602 | DTP | ester | —OH | n/a | B7 | ester |
| 603 | PBO | ester | —OH | n/a | B7 | ester |
| 604 | —OH | n/a | —OH | n/a | B7 | acetal |
| 605 | —OEt | ester | —OH | n/a | B7 | acetal |
| 606 | DTP | ester | —OH | n/a | B7 | acetal |
| 607 | PBO | ester | —OH | n/a | B7 | acetal |
| 608 | B8 | ester | —OH | n/a | —H | n/a |
| 609 | B8 | ester | —OEt | ester | —H | n/a |
| 610 | B8 | ester | DTP | ester | —H | n/a |
| 611 | B8 | ester | PBO | ester | —H | n/a |
| 612 | B8 | acetal | —OH | n/a | —H | n/a |
| 613 | B8 | acetal | —OEt | ester | —H | n/a |
| 614 | B8 | acetal | DTP | ester | —H | n/a |
| 615 | B8 | acetal | PBO | ester | —H | n/a |
| 616 | B8 | amide | —OH | n/a | —H | n/a |
| 617 | B8 | amide | —OEt | ester | —H | n/a |
| 618 | B8 | amide | DTP | ester | —H | n/a |
| 619 | B8 | amide | PBO | ester | —H | n/a |
| 620 | —OH | n/a | —OH | n/a | B8 | ester |
| 621 | —OEt | ester | —OH | n/a | B8 | ester |
| 622 | DTP | ester | —OH | n/a | B8 | ester |
| 623 | PBO | ester | —OH | n/a | B8 | ester |
| 624 | —OH | n/a | —OH | n/a | B8 | acetal |
| 625 | —OEt | ester | —OH | n/a | B8 | acetal |
| 626 | DTP | ester | —OH | n/a | B8 | acetal |
| 627 | PBO | ester | —OH | n/a | B8 | acetal |
| 628 | B9 | ester | —OH | n/a | —H | n/a |
| 629 | B9 | ester | —OEt | ester | —H | n/a |
| 630 | B9 | ester | DTP | ester | —H | n/a |
| 631 | B9 | ester | PBO | ester | —H | n/a |
| 632 | B9 | acetal | —OH | n/a | —H | n/a |
| 633 | B9 | acetal | —OEt | ester | —H | n/a |
| 634 | B9 | acetal | DTP | ester | —H | n/a |
| 635 | B9 | acetal | PBO | ester | —H | n/a |
| 636 | B9 | amide | —OH | n/a | —H | n/a |
| 637 | B9 | amide | —OEt | ester | —H | n/a |
| 638 | B9 | amide | DTP | ester | —H | n/a |
| 639 | B9 | amide | PBO | ester | —H | n/a |

TABLE 2-continued

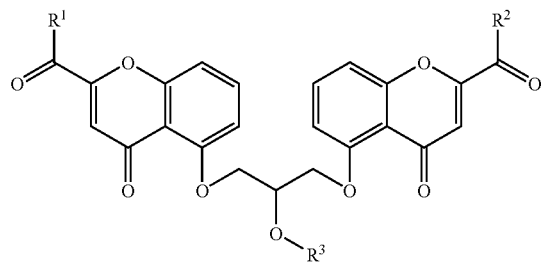
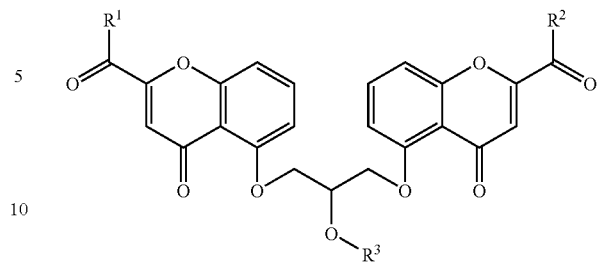

| Example # | R1 | linkage | R2 | linkage | R3 | linkage |
|---|---|---|---|---|---|---|
| 640 | —OH | n/a | —OH | n/a | B9 | ester |
| 641 | —OEt | ester | —OH | n/a | B9 | ester |
| 642 | DTP | ester | —OH | n/a | B9 | ester |
| 643 | PBO | ester | —OH | n/a | B9 | ester |
| 644 | —OH | n/a | —OH | n/a | B9 | acetal |
| 645 | —OEt | ester | —OH | n/a | B9 | acetal |
| 646 | DTP | ester | —OH | n/a | B9 | acetal |
| 647 | PBO | ester | —OH | n/a | B9 | acetal |
| 648 | B10 | ester | —OH | n/a | —H | n/a |
| 649 | B10 | ester | —OEt | ester | —H | n/a |
| 650 | B10 | ester | DTP | ester | —H | n/a |
| 651 | B10 | ester | PBO | ester | —H | n/a |
| 652 | B10 | acetal | —OH | n/a | —H | n/a |
| 653 | B10 | acetal | —OEt | ester | —H | n/a |
| 654 | B10 | acetal | DTP | ester | —H | n/a |
| 655 | B10 | acetal | PBO | ester | —H | n/a |
| 656 | B10 | amide | —OH | n/a | —H | n/a |
| 657 | B10 | amide | —OEt | ester | —H | n/a |
| 658 | B10 | amide | DTP | ester | —H | n/a |
| 659 | B10 | amide | PBO | ester | —H | n/a |
| 660 | —OH | n/a | —OH | n/a | B10 | ester |
| 661 | —OEt | ester | —OH | n/a | B10 | ester |
| 662 | DTP | ester | —OH | n/a | B10 | ester |
| 663 | PBO | ester | —OH | n/a | B10 | ester |
| 664 | —OH | n/a | —OH | n/a | B10 | acetal |
| 665 | —OEt | ester | —OH | n/a | B10 | acetal |
| 666 | DTP | ester | —OH | n/a | B10 | acetal |
| 667 | PBO | ester | —OH | n/a | B10 | acetal |
| 668 | B11 | ester | —OH | n/a | —H | n/a |
| 669 | B11 | ester | —OEt | ester | —H | n/a |
| 670 | B11 | ester | DTP | ester | —H | n/a |
| 671 | B11 | ester | PBO | ester | —H | n/a |
| 672 | B11 | acetal | —OH | n/a | —H | n/a |
| 673 | B11 | acetal | —OEt | ester | —H | n/a |
| 674 | B11 | acetal | DTP | ester | —H | n/a |
| 675 | B11 | acetal | PBO | ester | —H | n/a |
| 676 | B11 | amide | —OH | n/a | —H | n/a |
| 677 | B11 | amide | —OEt | ester | —H | n/a |
| 678 | B11 | amide | DTP | ester | —H | n/a |
| 679 | B11 | amide | PBO | ester | —H | n/a |
| 680 | —OH | n/a | —OH | n/a | B11 | ester |
| 681 | —OEt | ester | —OH | n/a | B11 | ester |
| 682 | DTP | ester | —OH | n/a | B11 | ester |
| 683 | PBO | ester | —OH | n/a | B11 | ester |
| 684 | —OH | n/a | —OH | n/a | B11 | acetal |
| 685 | —OEt | ester | —OH | n/a | B11 | acetal |
| 686 | DTP | ester | —OH | n/a | B11 | acetal |
| 687 | PBO | ester | —OH | n/a | B11 | acetal |
| 688 | B12 | ester | —OH | n/a | —H | n/a |
| 689 | B12 | ester | —OEt | ester | —H | n/a |
| 690 | B12 | ester | DTP | ester | —H | n/a |
| 691 | B12 | ester | PBO | ester | —H | n/a |
| 692 | B12 | acetal | —OH | n/a | —H | n/a |
| 693 | B12 | acetal | —OEt | ester | —H | n/a |
| 694 | B12 | acetal | DTP | ester | —H | n/a |
| 695 | B12 | acetal | PBO | ester | —H | n/a |
| 696 | B12 | amide | —OH | n/a | —H | n/a |
| 697 | B12 | amide | —OEt | ester | —H | n/a |
| 698 | B12 | amide | DTP | ester | —H | n/a |
| 699 | B12 | amide | PBO | ester | —H | n/a |
| 700 | —OH | n/a | —OH | n/a | B12 | ester |
| 701 | —OEt | ester | —OH | n/a | B12 | ester |
| 702 | DTP | ester | —OH | n/a | B12 | ester |
| 703 | PBO | ester | —OH | n/a | B12 | ester |
| 704 | —OH | n/a | —OH | n/a | B12 | acetal |
| 705 | —OEt | ester | —OH | n/a | B12 | acetal |
| 706 | DTP | ester | —OH | n/a | B12 | acetal |
| 707 | PBO | ester | —OH | n/a | B12 | acetal |
| 708 | B13 | ester | —OH | n/a | —H | n/a |
| 709 | B13 | ester | —OEt | ester | —H | n/a |
| 710 | B13 | ester | DTP | ester | —H | n/a |
| 711 | B13 | ester | PBO | ester | —H | n/a |
| 712 | B13 | acetal | —OH | n/a | —H | n/a |
| 713 | B13 | acetal | —OEt | ester | —H | n/a |
| 714 | B13 | acetal | DTP | ester | —H | n/a |
| 715 | B13 | acetal | PBO | ester | —H | n/a |
| 716 | B13 | amide | —OH | n/a | —H | n/a |
| 717 | B13 | amide | —OEt | ester | —H | n/a |
| 718 | B13 | amide | DTP | ester | —H | n/a |
| 719 | B13 | amide | PBO | ester | —H | n/a |
| 720 | —OH | n/a | —OH | n/a | B13 | ester |
| 721 | —OEt | ester | —OH | n/a | B13 | ester |
| 722 | DTP | ester | —OH | n/a | B13 | ester |
| 723 | PBO | ester | —OH | n/a | B13 | ester |
| 724 | —OH | n/a | —OH | n/a | B13 | acetal |
| 725 | —OEt | ester | —OH | n/a | B13 | acetal |
| 726 | DTP | ester | —OH | n/a | B13 | acetal |
| 727 | PBO | ester | —OH | n/a | B13 | acetal |
| 728 | B14 | amide | —OH | n/a | —H | n/a |
| 729 | B14 | amide | —OEt | ester | —H | n/a |
| 730 | B14 | amide | DTP | ester | —H | n/a |
| 731 | B14 | amide | PBO | ester | —H | n/a |
| 732 | B15 | amide | —OH | n/a | —H | n/a |
| 733 | B15 | amide | —OEt | ester | —H | n/a |
| 734 | B15 | amide | DTP | ester | —H | n/a |
| 735 | B15 | amide | PBO | ester | —H | n/a |
| 736 | B16 | amide | —OH | n/a | —H | n/a |
| 737 | B16 | amide | —OEt | ester | —H | n/a |
| 738 | B16 | amide | DTP | ester | —H | n/a |
| 739 | B16 | amide | PBO | ester | —H | n/a |
| 740 | B17 | amide | —OH | n/a | —H | n/a |
| 741 | B17 | amide | —OEt | ester | —H | n/a |
| 742 | B17 | amide | DTP | ester | —H | n/a |
| 743 | B17 | amide | PBO | ester | —H | n/a |
| 744 | B18 | amide | —OH | n/a | —H | n/a |
| 745 | B18 | amide | —OEt | ester | —H | n/a |
| 746 | B18 | amide | DTP | ester | —H | n/a |
| 747 | B18 | amide | PBO | ester | —H | n/a |
| 748 | B19 | amide | —OH | n/a | —H | n/a |
| 749 | B19 | amide | —OEt | ester | —H | n/a |
| 750 | B19 | amide | DTP | ester | —H | n/a |
| 751 | B19 | amide | PBO | ester | —H | n/a |
| 752 | B20 | amide | —OH | n/a | —H | n/a |
| 753 | B20 | amide | —OEt | ester | —H | n/a |
| 754 | B20 | amide | DTP | ester | —H | n/a |
| 755 | B20 | amide | PBO | ester | —H | n/a |
| 756 | B21 | amide | —OH | n/a | —H | n/a |
| 757 | B21 | amide | —OEt | ester | —H | n/a |
| 758 | B21 | amide | DTP | ester | —H | n/a |
| 759 | B21 | amide | PBO | ester | —H | n/a |
| 760 | B22 | amide | —OH | n/a | —H | n/a |
| 761 | B22 | amide | —OEt | ester | —H | n/a |
| 762 | B22 | amide | DTP | ester | —H | n/a |
| 763 | B22 | amide | PBO | ester | —H | n/a |
| 764 | B23 | amide | —OH | n/a | —H | n/a |
| 765 | B23 | amide | —OEt | ester | —H | n/a |
| 766 | B23 | amide | DTP | ester | —H | n/a |
| 767 | B23 | amide | PBO | ester | —H | n/a |

TABLE 2-continued

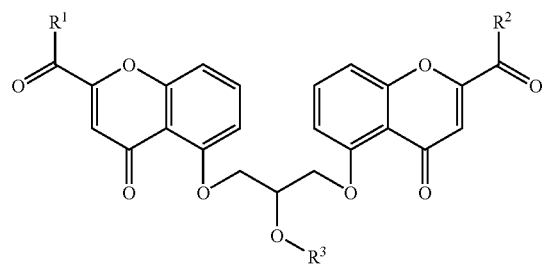

| Example # | R1 | linkage | R2 | linkage | R3 | linkage |
|---|---|---|---|---|---|---|
| 768 | B24 | ester | —OH | n/a | —H | n/a |
| 769 | B24 | ester | —OEt | ester | —H | n/a |
| 770 | B24 | ester | DTP | ester | —H | n/a |
| 771 | B24 | ester | PBO | ester | —H | n/a |
| 772 | —OH | n/a | —OH | n/a | B24 | acetal |
| 773 | —OEt | ester | —OH | n/a | B24 | acetal |

TABLE 2-continued

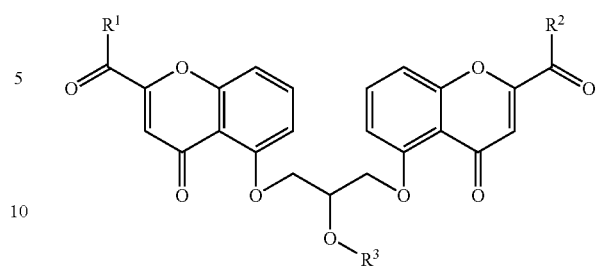

| Example # | R1 | linkage | R2 | linkage | R3 | linkage |
|---|---|---|---|---|---|---|
| 774 | DTP | ester | —OH | n/a | B24 | acetal |
| 775 | PBO | ester | —OH | n/a | B24 | acetal |

Some additional compounds of the invention are shown below to illustrate various further aspects of the invention:

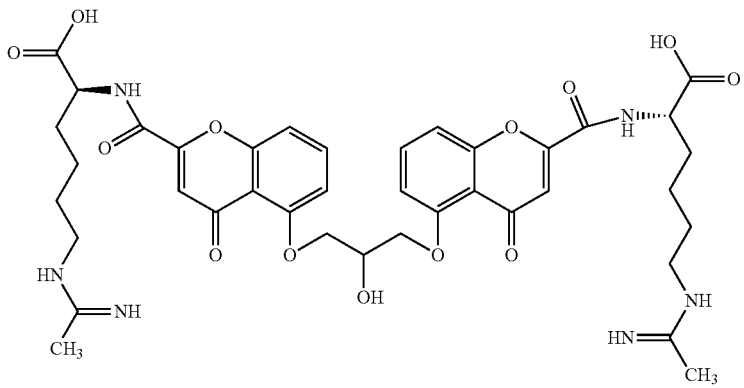

900

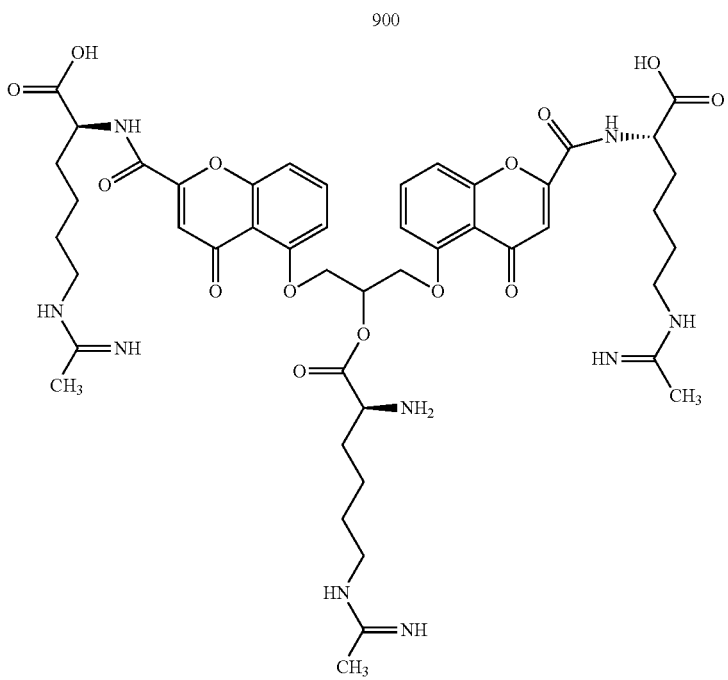

901

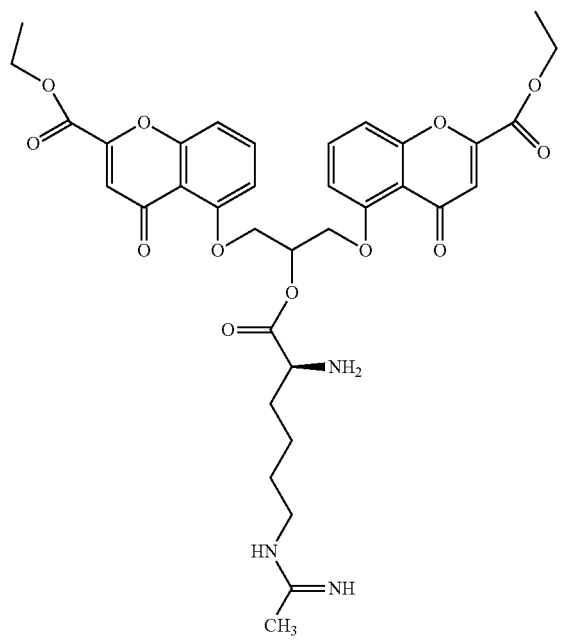
902
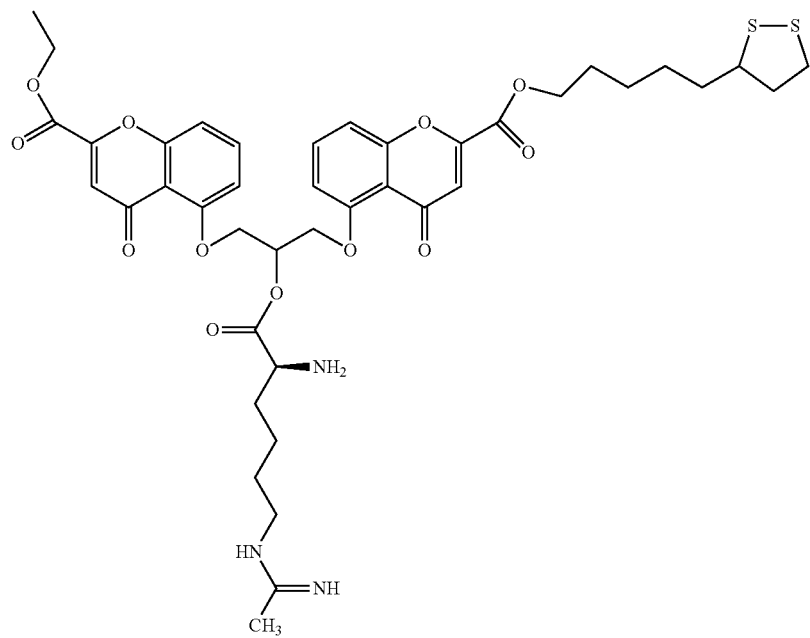
903

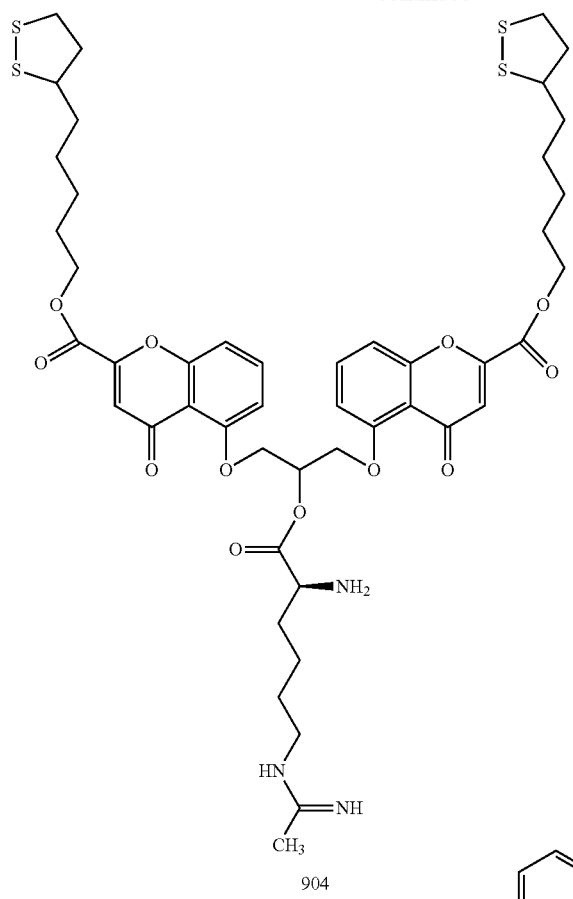
904
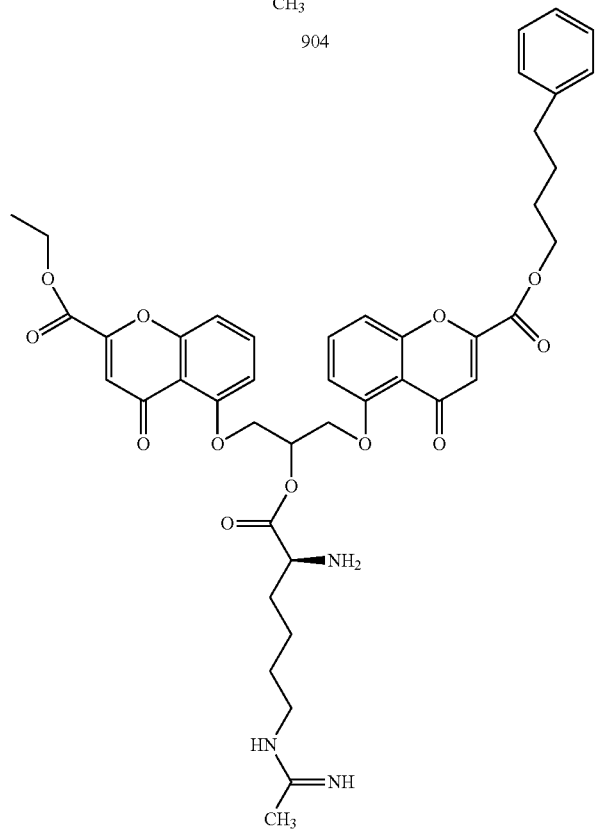
905

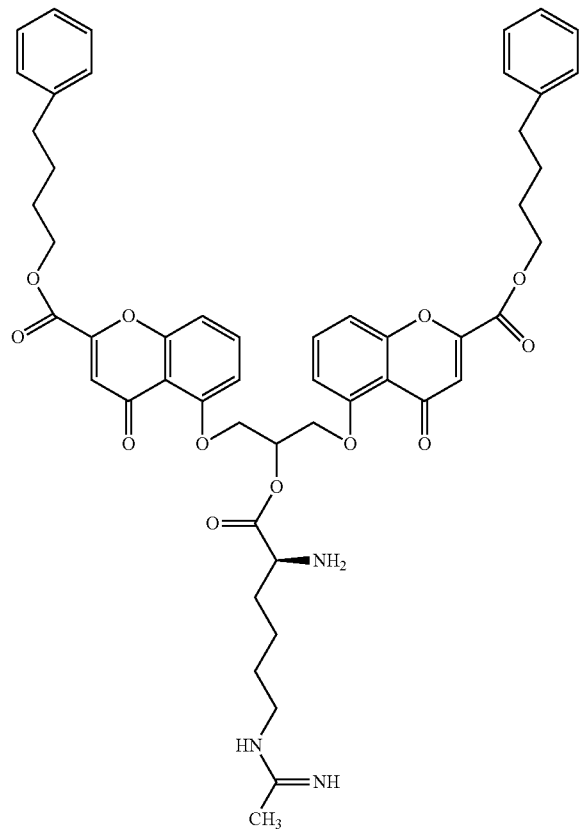
906
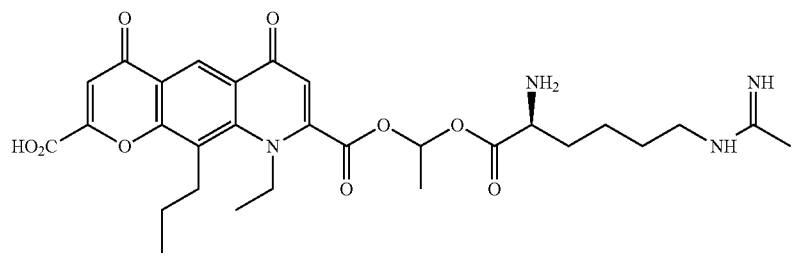
907
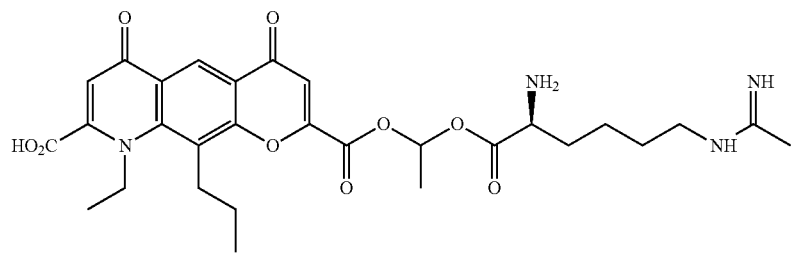
908

Example 900 illustrates two iNOS inhibitors attached to a single cromolyn core. In this particular example, both iNOS inhibitors are the same, but that is not a requirement of the invention. Similarly, without intending to so restrict the invention, example 901 illustrates three iNOS inhibitors attached to a single cromolyn core. Examples 902-906 illustrate various mixed esters. Examples 907 and 908 illustrate acetals of acetaldehyde (whereas the examples in Tables 1 and 2 show acetals of formaldehyde); both acetals of acetaldehyde and acetals of formaldehyde are within the scope of the invention, and each of the formaldehyde acetal examples in the tables has a corresponding acetaldehyde acetal example.

The invention claimed is:

1. A compound of formula I

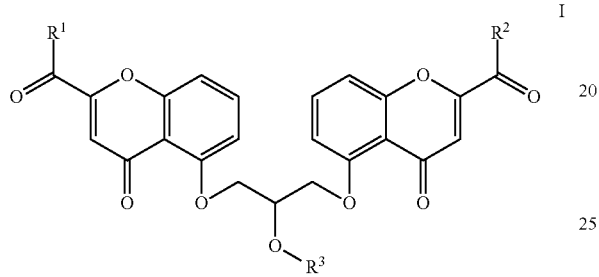

wherein
R$^1$ and R$^2$ are chosen from hydroxy, C$_1$, C$_2$, C$_3$, C$_4$, C$_5$, and C$_6$ straight and branched alkoxy, -G-O(C=O)R$^4$, R$^5$, —NHR$^6$, —OR$^7$ and —O$^-$X$^+$, wherein X$^+$ is a pharmaceutically acceptable cation;
R$^3$ is chosen from hydrogen, —(C=O)R$^4$, —(C=O)-G-O(C=O)R$^4$, —(C=O)R$^5$, —(C=O)NHR$^6$ and —(C=O)OR$^7$;
—O(C=O)R$^4$ is the deshydrogen residue of a carboxylic acid, the parent of which, R$^4$COOH, is chosen from the group consisting of:

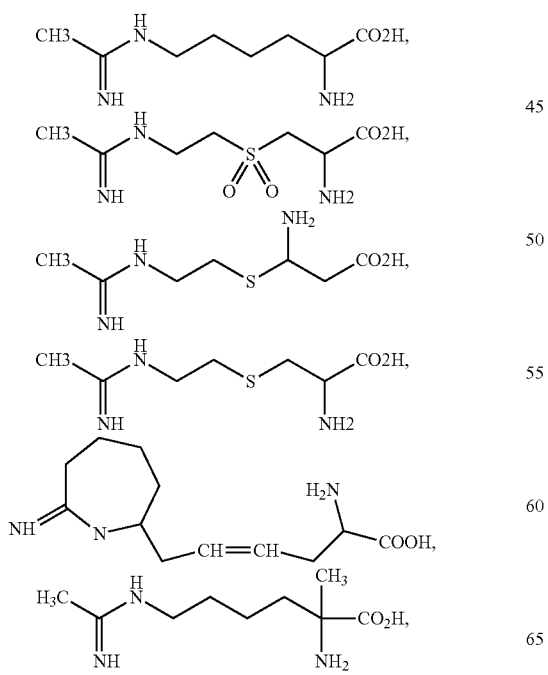

—(C=O)R$^4$ is the deshydroxy residue of a carboxylic acid, the parent of which, R$^4$COOH, is chosen from the group consisting of:

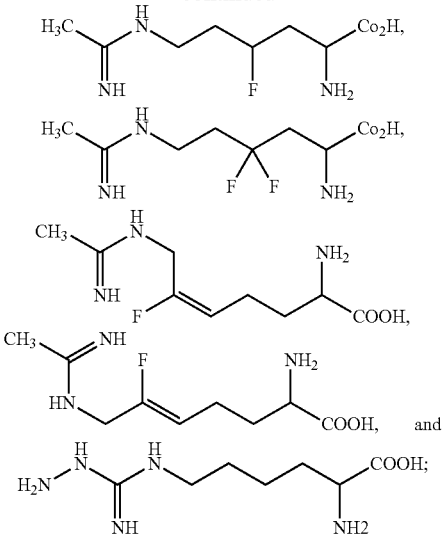

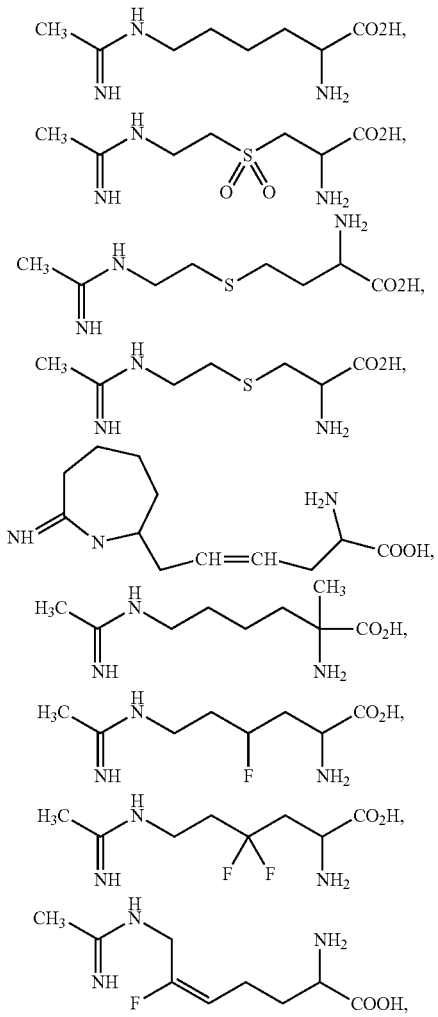

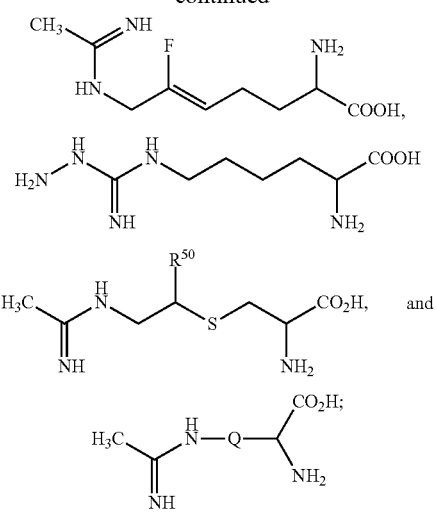
$R^5$ is —O—$R^{20}$—U, wherein U is chosen from hydrogen, (1,2-dithiolan-3-yl) and phenyl, and $R^{20}$ is a divalent $C_1$ to $C_{20}$ alkane or oxaalkane residue;
—$NHR^6$ is the deshydrogen residue of an amine, the parent of which, $R^6NH_2$, is chosen from the group consisting of:
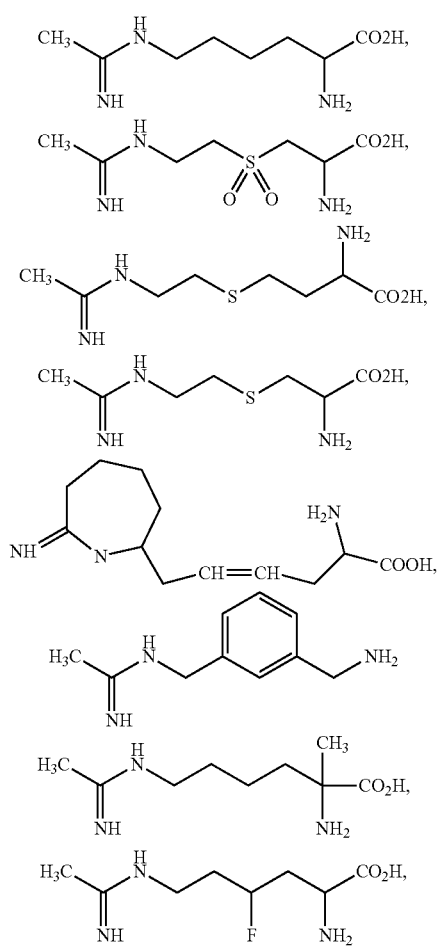
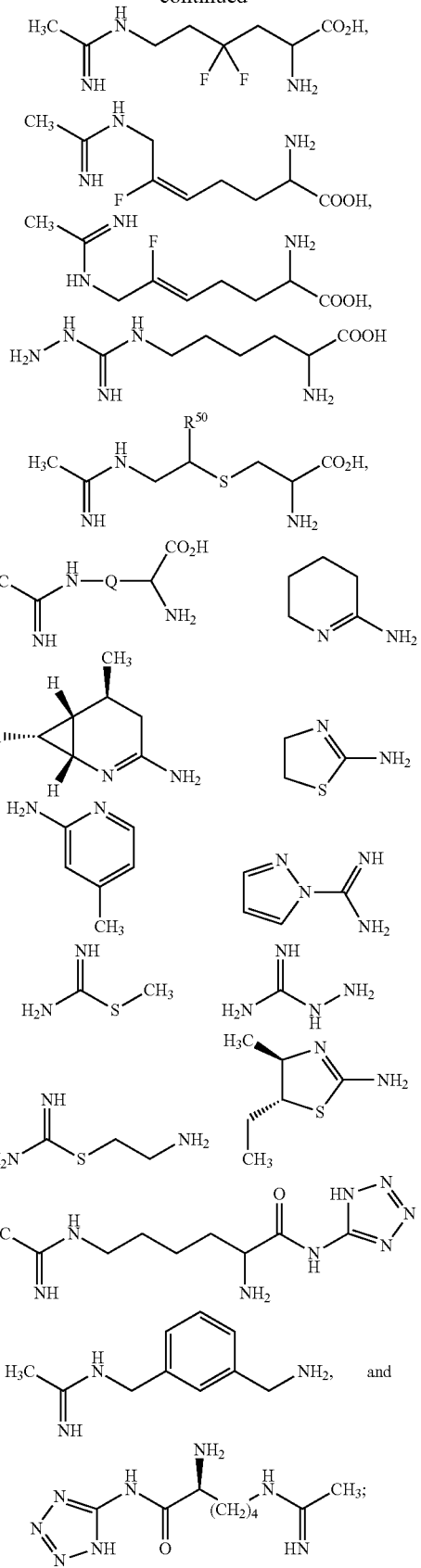

—OR⁷ is

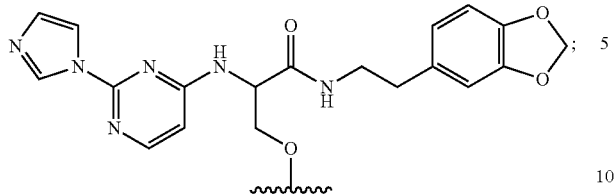

G is chosen from —OCH₂— and —OCH(CH₃)—;
at least one of $R^1$, $R^2$ and $R^3$ must be -G-O(C=O)R⁴, —NHR⁶, —OR⁷, —(C=O)R⁴, —(C=O)-G-O(C=O)R⁴, —(C=O)R⁵, —(C=O)NHR⁶ or —(C=O)OR⁷
$R^{50}$ is chosen from $C_1$ to $C_4$ alkyl, $C_3$ to $C_4$ cycloalkyl, $C_1$ to $C_4$ hydroxyalkyl and $C_1$ to $C_4$ haloalkyl;
Q is chosen from —CH₂CH=CHCH₂—, —(CH₂)$_p$X(CH₂)$_q$—, —O—, —NR⁵¹— and —(CH₂)$_r$A(CH₂)$_s$—;
p is 2 or 3;
q is 1 or 2;
X is S(O)$_x$;
x is 0, 1 or 2;
$R^{51}$ is H or $C_{1-6}$ alkyl;
r is 1 or 2;
s is 1 or 2; and
A is cyclobutyl, phenyl or pyridyl.

2. A compound according to claim 1 wherein R⁴COOH and R⁶NH₂ are chosen from:

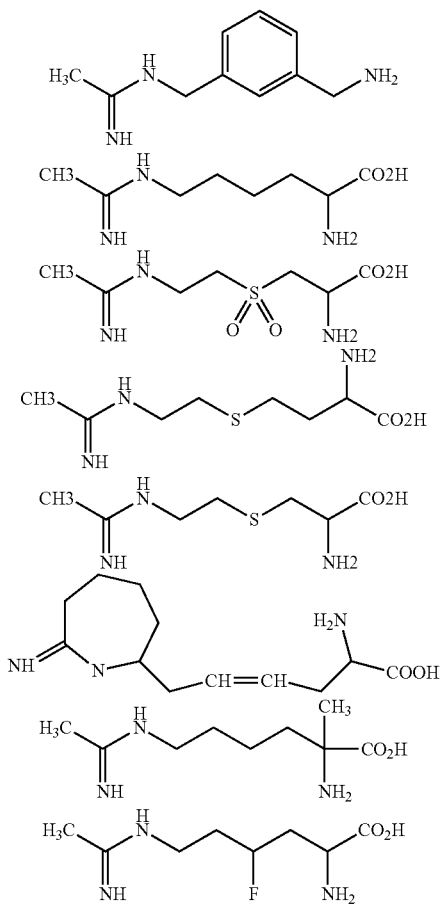

3. A compound according to claim 1 wherein R⁴COOH and R⁶NH₂ are chosen from compounds of structure:

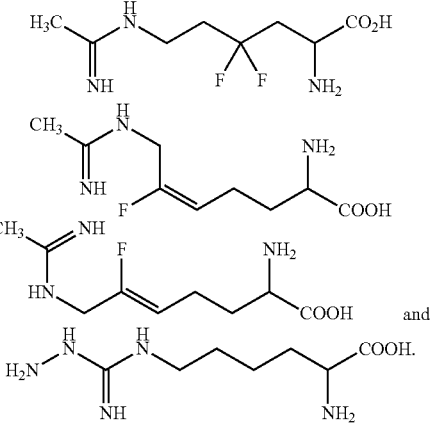

wherein $R^{50}$ is chosen from $C_1$ to $C_4$ alkyl, $C_3$ to $C_4$ cycloalkyl, $C_1$ to $C_4$ hydroxyalkyl and $C_1$ to $C_4$ haloalkyl.

4. A compound according to claim 1 wherein R⁴COOH and R⁶NH₂ are chosen from compounds of structure:

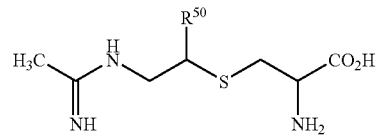

wherein Q is chosen from —CH₂CH=CHCH₂—, —(CH₂)$_p$X(CH₂)$_q$—, —O—, —NR⁵¹— and —(CH₂)$_r$A(CH₂)$_s$—;
p is 2 or 3;
q is 1 or 2;
X is S(O)$_x$;
x is 0, 1 or 2;
$R^{51}$ is H or $C_{1-6}$ alkyl;
r is 1 or 2;
s is 1 or 2; and
A is cyclobutyl, phenyl or pyridyl.

5. A compound according to claim 1 wherein R⁶NH₂ is chosen from compounds of structure:

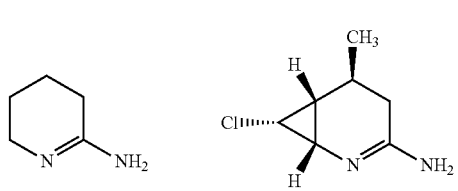

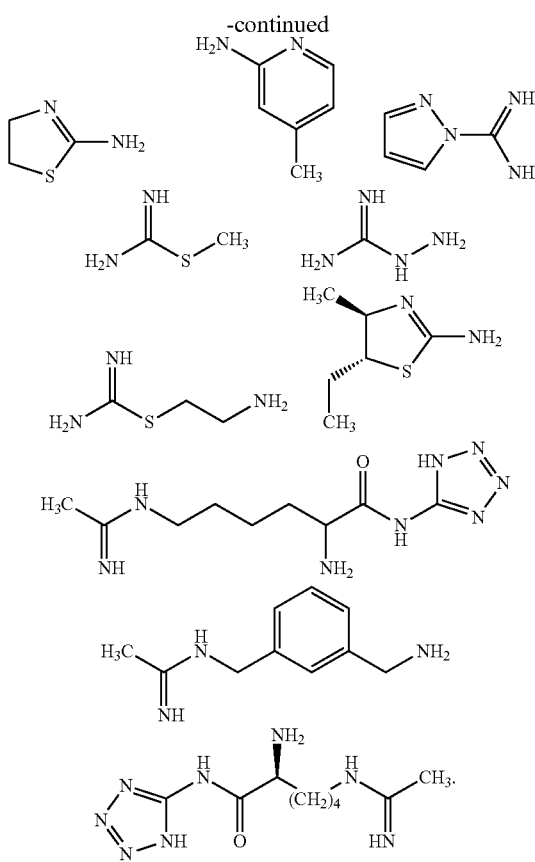

6. A compound according to claim 1 wherein $R^1$ and $R^2$ are chosen from hydroxy, $C_1$, $C_2$, $C_3$, $C_4$, $C_5$, and $C_6$ straight and branched alkoxy, —$R^5$, —$NHR^6$, —$OR^7$ and —$O^-X^+$; and $R^3$ is chosen from hydrogen, —(C=O)$R^4$, —(C=O)$R^5$, —(C=O)$NHR^6$ and —(C=O)$OR^7$.

7. A compound according to claim 1 wherein at least one of $R^1$, $R^2$ and $R^3$ is -G-O(C=O)$R^4$ or —(C=O)-G-O(C=O)$R^4$; and G is chosen from —OCH$_2$— and —OCH(CH$_3$)—.

8. A compound according to claim 1 wherein $R^5$ is

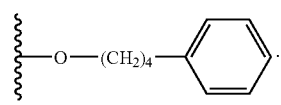

9. A compound according to claim 1 wherein $R^5$ is

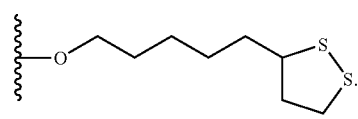

10. A compound according to claim 1 of formula

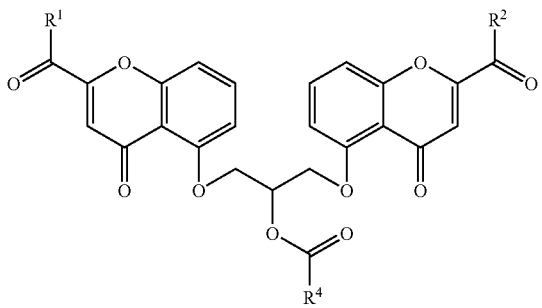

wherein $R^1$ and $R^2$ are chosen from hydroxy, $C_1$, $C_2$, $C_3$, $C_4$, $C_5$, and $C_6$ straight and branched alkoxy and —$O^-X^+$.

11. A compound according to claim 1 of formula:

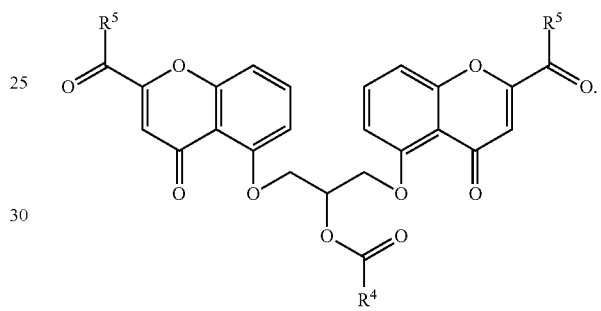

12. A compound according to claim 1 of formula:

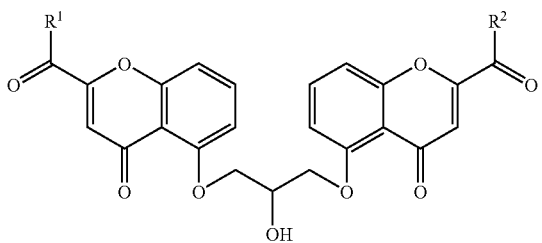

wherein $R^1$ is chosen from -G-O(C=O)$R^4$, —$NHR^6$ and $OR^7$; and
$R^2$ is chosen from hydroxy, $C_1$, $C_2$, $C_3$, $C_4$, $C_5$, and $C_6$ straight and branched alkoxy, $R^5$ and —$O^-X$.

13. A pharmaceutical composition comprising a pharmaceutically acceptable carrier and a compound according to claim 1.

14. An aerosol pharmaceutical composition according to claim 13.

15. An oral pharmaceutical composition according to claim 13.

16. An oral pharmaceutical composition according to claim 15 in the form of a tablet, capsule or syrup.

* * * * *